US008828670B2

(12) United States Patent
Merk et al.

(10) Patent No.: US 8,828,670 B2
(45) Date of Patent: Sep. 9, 2014

(54) METHOD FOR THE PRODUCTION OF PROTEINS AND PEPTIDES

(75) Inventors: Helmut Merk, Berlin (DE); Wolfgang Stiege, Berlin (DE); Christine Gless, Berlin (DE); Michael Gerrits, Berlin (DE)

(73) Assignee: RiNA Netzwerk RNA Technologien GmbH, Berlin (DE)

( * ) Notice: Subject to any disclaimer, the term of this patent is extended or adjusted under 35 U.S.C. 154(b) by 0 days.

(21) Appl. No.: 13/545,364

(22) Filed: Jul. 10, 2012

(65) Prior Publication Data

US 2013/0017576 A1     Jan. 17, 2013

(30) Foreign Application Priority Data

Jul. 11, 2011  (DE) .................. 10 2011 107 562

(51) Int. Cl.
*A61K 39/00*     (2006.01)
(52) U.S. Cl.
USPC ... 435/7.1; 435/70.21; 530/387.3; 530/391.1; 530/388.1; 424/133.1; 424/135.1; 424/139.1; 424/179.1; 536/23.53

(58) Field of Classification Search
CPC combination set(s) only.
See application file for complete search history.

(56) References Cited

FOREIGN PATENT DOCUMENTS

DE        102004032460        6/2004

OTHER PUBLICATIONS

Lynn Litterer et al (Expressing Mammalian Proteins Using Insect and Rabbit Cell-Free Lysates. Promega Cell-Free Expression Feb. 2009.*
Hideki Yamaji. Production of functional antibody Fab fragment by recombinant insect cells Biochemical Engineering Journal 41 (2008) 203-209.*
Nilsang S, Nandakumar KS, Galaev IY, Rakshit SK, Holmdahl R, Mattiasson B, Kumar A., "Monoclonal antibody production using a new supermacroporous cryogel bioreactor". Biotechnol Prog 23:932-939, (2007).
Rodrigues ME, Costa AR, Henriques M, Azeredo J, Oliveira R, "Technological progresses in monoclonal antibody production systems", Biotechnol Prog 26:332-51, (2010).
Humphreys DP, "Production of antibodies and antibody fragments in *Escherichia coli* and a comparison of their functions, uses and modification", Curr Opin Drug Discov Devel 6:188-196, (2003).
Hoogenboom HR, "Selecting and screening recombinant antibody libraries", Nat Biotechnol 23:1105-1116, (2005).
Spirin AS, Baranov VI, Ryabova LA, Ovodov SY, Alakhov YB, "A continuous cell-free translation system capable of producing polypeptides in high yield", Science 242:1162-4, (1988).
Kim TW, Oh IS, Keum JW, Kwon YC, Byun JY, Lee KH, Choi CY, Kim DM, "Prolonged cell-free protein synthesis using dual energy sources: Combined use of creatine phosphate and glucose for the efficient supply of ATP and retarded accumulation of phosphate", Biotechnol Bioeng 97:1510-1515, (2007).
Madin K, Sawasaki T, Ogasawara T, Endo Y, "A highly efficient and robust cell-free protein synthesis system prepared from wheat embryos: plants apparently contain a suicide system directed at ribosomes", Proc Natl Acad Sci, USA, vol. 97(2): 559-564, (2000).
Tsuboi T, Takeo S, Iriko H, Jin L, Tsuchimochi M, Matsuda S, Han E, Otsuk, H, Kaneko O, Sattabongkot J, Udomsangpetch R, Sawasaki T, Tori, M, Endo, Y, "Wheat germ Cell-Free System-Based Production of Malaria Proteins for Discovery of Novel Vaccine Candidate", Infection and Immunity 1702-1708, (2008).
Tarui H, Murata M, Tani I, Imanishi S, Nishikawa S, Hara T. "Establishment and characterization of cell-free translation/glycosylation in insect cell (*Spodoptera frugiperda* 21) extract prepared with high pressure treatment", Appl Microbiol Biotechnol, 55:446-453, (2001).
Kubick S, Schacherl J, Fleischer-Notter H, Royall E, Roberts LO, Stiege W, "In vitro Translation in an Insect-Based Cell-Free System", In: Swartz, J.R. (Ed.) Cell-Free Protein Expression. Springer, Berlin Heidelberg New York, 209-217, (2003).
Mikami S, Masutani M, Sonenberg N, Yokoyama S, Imataka H, "An efficient mammalian cell-free translation system supplemented with translation factors", Protein Expr Purif 46(2): 348-357, (2006).
Ryabova LA, Desplancq D, Spirin AS, Pluckthun A, "Functional antibody production using cell-free translation: effects of protein disulfide isomerase and chaperones", Nat Biotechnol 15:79-84, (1997).
Merk H, Stiege W, Tsumoto K, Kumagai I, Erdmann VA, "Cell-free Expression of two Single-Chain Monoclonal Antibodies against Lysozyme: Effect of Domain Arrangement on the Expression", J Biochem 125:328-333, (1999).
Tsumoto K, Nakaoki Y, Ueda Y, Ogasahara K, Yutani K, Watanabe K, Kumagai I, "Effect of the order of antibody variable regions on the expression of the single-chain HyHEL10 Fv fragment in *E. coli* and the thermodynamic analysis of its antigen-binding properties", Biochem Biophys Res Commun 201:546-51, (1994).
Oh IS, Lee JC, Lee MS, Chung JH, Kim DM, "Cell-free production of functional antibody fragments", Bioprocess Biosyst Eng 33:127-32, (2010).
Kim DM, Swartz JR, "Efficient production of a bioactive, multiple disulfide-bonded protein using modified extracts of *Escherichia coli*", Biotechnol Bioeng 85:122-9, (2004).
Oh IS, Kim DM, Kim TW, Park CG, Chloi CY, "Providing an oxidizing environment for the cell-free expression of disulfide-containing proteins by exhausting the reducing activity of *Escherichia coli* S30 extract", Biotechnol Prog 22:1225-8, (2006).

\* cited by examiner

*Primary Examiner* — Kagnew H Gebreyesus
(74) *Attorney, Agent, or Firm* — Ann Wieczorek; Karin L. Williams; Mayer & Williams PC

(57) ABSTRACT

The invention relates to a method for producing monomeric or dimeric proteins or peptides containing internal or external disulfide bonds, comprising the following steps: a) a cell-free lysate, obtainable from eukaryotic cells, is provided, which contains functional microsomal vesicles, b) a nucleic acid coding the protein or peptide and additionally containing a signal sequence is added to the lysate, c) the lysate with the nucleic acid is held for a given time at a temperature in the range from 20 to 35° C., proteins or peptides formed with the nucleic acid being translocated into the microsomal vesicles, d) the microsomal vesicles are then dissolved, and the proteins or peptides obtained thereby are optionally separated from the lysate.

8 Claims, 10 Drawing Sheets

METHOD FOR THE PRODUCTION OF PROTEINS AND PEPTIDES

FIELD OF THE INVENTION

The invention relates to a method for producing monomeric or dimeric proteins or peptides containing internal or external disulfide bonds, comprising the following steps: a) a cell-free lysate is provided, b) a nucleic acid coding the protein or peptide is added to the lysate, c) the lysate with the nucleic acid is held for a given time at a temperature in the range from 20 to 35° C., d) the proteins or peptides obtained thereby are optionally separated from the lysate. The invention further relates to proteins or peptides obtainable by such a method and to a preparation obtainable by such a method.

PRIOR ART AND BACKGROUND OF THE INVENTION

Monoclonal antibodies are used in a wide field of applications also including the use as research tools and for diagnostic and therapeutic purposes.

Since scFv (single-chain variable fragment) and Fab (antigen-binding fragment) as parts of complete antibodies are small and expressible in *Escherichia coli* and permit a systematic survey and a selection for molecules binding with high affinity, the potential range of applications of these molecules quickly widens. One of the most important limitations of this widening is however the speed of the generation and the analysis of the efficiency of the bond and the effects of antibodies on their target molecules. An acceleration of the antibody production would permit a faster response to health risks caused by a pandemic spread of pathogenic viruses and microorganisms.

The conventional production of antibodies occurs by the culture of animal cells (Nilsang S, Nandakumar K S, Galaev I Y, Rakshit S K, Holmdahl R, Mattiasson B, Kumar A. (2007) Monoclonal antibody production using a new supermacroporous cryogel bioreactor. Biotechnol Prog 23:932-939; Rodrigues M E, Costa A R, Henriques M, Azeredo J, Oliveira R (2010) Technological progresses in monoclonal antibody production systems. Biotechnol Prog 2:332-51). A distinct acceleration and a more economic production of antibodies could be achieved in recent years by the expression thereof in *Escherichia coli* cells (Humphreys D P (2003) Production of antibodies and antibody fragments in *Escherichia coli* and a comparison of their functions, uses and modification. Curr Opin Drug Discov Devel 6:188-196). Cell-based methods of the antibody production require however a time and work-intensive cell culture execution. For a bacterial expression, furthermore additional efforts are necessary for cloning the expressible matrices coding for antibodies (Hoogenboom H R (2005) Selecting and screening recombinant antibody libraries. Nat Biotechnol 23:1105-1116).

Meanwhile, the cell-free protein expression is regarded as a promising alternative for overcoming the limitations of cell-based methods. One reason for this is the significant improvement of the productivity, economy and the activity of the synthesized proteins in cell-free prokaryotic systems achieved in recent years (Spirin A S, Baranov V I, Ryabova L A, Ovodov S Y, Alakhov Y B (1988) A continuous cell-free translation system capable of producing polypeptides in high yield. Science 242:1162-4; Strey J, Merk H, Stiege W (2004) Verfahren zur präparativen in vitro Proteinbiosynthese. Patent DE 102004032460; Kim T W, Oh I S, Keum J W, Kwon Y C, Byun J Y, Lee K H, Choi C Y, Kim D M (2007) Prolonged cell-free protein synthesis using dual energy sources: combined use of creatine phosphate and glucose for the efficient supply of ATP and retarded accumulation of phosphate. Biotechnol Bioeng 97:1510-1515) and eukaryotic systems (Madin K, Sawasaki T, Ogasawara T, Endo Y (2000) A highly efficient and robust cell-free protein synthesis system prepared from wheat embryos: plants apparently contain a suicide system directed at ribosomes. Proc Natl Acad Sci USA 97(2):559-564; Tsuboi T, Takeo S, Iriko H, Jin L, Tsuchimochi M, Matsuda S, Han E, Otsuk, H, Kaneko O, Sattabongkot J, Udomsangpetch R, Sawasaki T, Tori, M, Endo, Y (2008) Wheat germ Cell-Free System-Based Production of Malaria Proteins for Discovery of Novel Vaccine Candidates. Infection and Immunity 1702-1708; Tarui H, Murata M, Tani I, Imanishi S, Nishikawa S, Hara T (2001) Establishment and characterization of cell-free translation/glycosylation in insect cell (*Spodoptera frugiperda* 21) extract prepared with high pressure treatment. Appl Microbiol Biotechnol 55:446-453; Kubick S, Schacherl J, Fleischer-Notter H, Royall E, Roberts L O, Stiege W (2003) In vitro Translation in an Insect-Based Cell-Free System. In: Swartz, J. R. (Ed.) Cell-Free Protein Expression. Springer, Berlin Heidelberg New York, 209-217; Mikami S, Masutani M, Sonenberg N, Yokoyama S, Imataka H (2006) An efficient mammalian cell-free translation system supplemented with translation factors. Protein Expr Purif 46(2):348-357). Modifications of some of these systems permitted the synthesis of disulfide-bonded proteins including scFv (single-chain antibody) (Ryabova L A, Desplancq D, Spirin A S, Pluckthun A (1997) Functional antibody production using cell-free translation: effects of protein disulfide isomerase and chaperones. Nat Biotechnol 15:79-84; Merk H, Stiege W, Tsumoto K, Kumagai I, Erdmann V A (1999) Cell-free Expression of two Single-Chain Monoclonal Antibodies against Lysozyme: Effect of Domain Arrangement on the Expression. J Biochem 125:328-333). Fab antibody fragments are however more attractive, due to their better binding properties, than scFv. Recently, the cell-free expression of a Fab in a system based on *E. coli* was shown (Oh I S, Lee J C, Lee M S, Chung J H, Kim D M (2010) Cell-free production of functional antibody fragments. Bioprocess Biosyst Eng 33:127-32).

The drawbacks of the cell-free systems based on *E. coli* are however a low specific activity of the produced Fab and the necessity of the removal von toxins of the expression system, before the synthesized Fab can be used for a cell-based quality test. *E. coli* systems meanwhile offer in their simple version (batch system) synthesis performances of up to 1 milligram newly synthesized protein per milliliter reaction solution. The highest value for the yield of functional Fab from a cell-free system is however only 30 µg/ml (Oh I S, Lee J C, Lee M S, Chung J H, Kim D M (2010) Cell-free production of functional antibody fragments. Bioprocess Biosyst Eng 33:127-32). In spite of the high productivity of the cell-free *E. coli* system, thus only a fraction of the synthesized protein can be used. Furthermore, in order to obtain precise measurement results, the active portion of the synthesized protein must be separated from the inactive portion, which means more efforts for this cleaning step.

Cell-free systems based on *E. coli* have high activities, which during the reaction will substantially vary the redox potential. This variation reduces the activity of the synthesized antibody fragments. A reduction of the variation of the redox potential was achieved by chemical pre-treatment of the cell lysate, Kim D M, Swartz J R (2004) Efficient production of a bioactive, multiple disulfide-bonded protein using modified extracts of *Escherichia coli*. Biotechnol Bioeng 85:122-9; Oh I S, Kim D M, Kim T W, Park C G, Chloi C Y (2006) Providing an oxidizing environment for the cell-free expression of disulfide-containing proteins by exhausting the reducing activity of *Escherichia coli* S30 extract. Biotechnol Prog 22:1225-89. This is however disadvantageous for the handling of the system, since another step is required, which furthermore can be automated with additional efforts only.

In order to be able to synthesize in *E. coli*-based cell-free systems noteworthy concentrations of soluble and active antibody fragment, they are supplemented with chaperones, for instance GroE, DnaK and protein disulfide isomerase, for instance PDI, DsbC (Ryabova L A, Desplancq D, Spirin A S, Pluckthun A (1997) Functional antibody production using cell-free translation: effects of protein disulfide isomerase and chaperones. Nat Biotechnol 15:79-84; Merk H, Stiege W, Tsumoto K, Kumagai I, Erdmann V A (1999) Cell-free Expression of two Single-Chain Monoclonal Antibodies against Lysozyme: Effect of Domain Arrangement on the Expression. J Biochem 125:328-333; Tsumoto K, Nakaoki Y, Ueda Y, Ogasahara K, Yutani K, Watanabe K, Kumagai I (1994) Effect of the order of antibody variable regions on the expression of the single-chain HyHEL10 Fv fragment in *E. coli* and the thermodynamic analysis of its antigen-binding properties. Biochem Biophys Res Commun 201:546-51; Oh I S, Lee J C, Lee M S, Chung J H, Kim D M (2010) Cell-free production of functional antibody fragments. Bioprocess Biosyst Eng 33:127-32; Kim D M, Swartz J R (2004) Efficient production of a bioactive, multiple disulfide-bonded protein using modified extracts of *Escherichia coli*. Biotechnol Bioeng 85:122-9; Oh I S, Kim D M, Kim T W, Park C G, Chloi C Y (2006) Providing an oxidizing environment for the cell-free expression of disulfide-containing proteins by exhausting the reducing activity of *Escherichia coli* S30 extract. Biotechnol Prog 22:1225-8).

TECHNICAL OBJECT OF THE INVENTION

It is therefore the technical object of the invention to propose a method for producing proteins and peptides, in particular antibodies or antibody fragments, wherein the obtained proteins or peptides have an improved highly specific activity and simultaneously the synthesis effort is reduced, in particular also with regard to the used nucleic acid and the post-treatment of the obtained proteins or peptides.

BASICS OF THE INVENTION AND PREFERRED EMBODIMENTS

Figure 1:
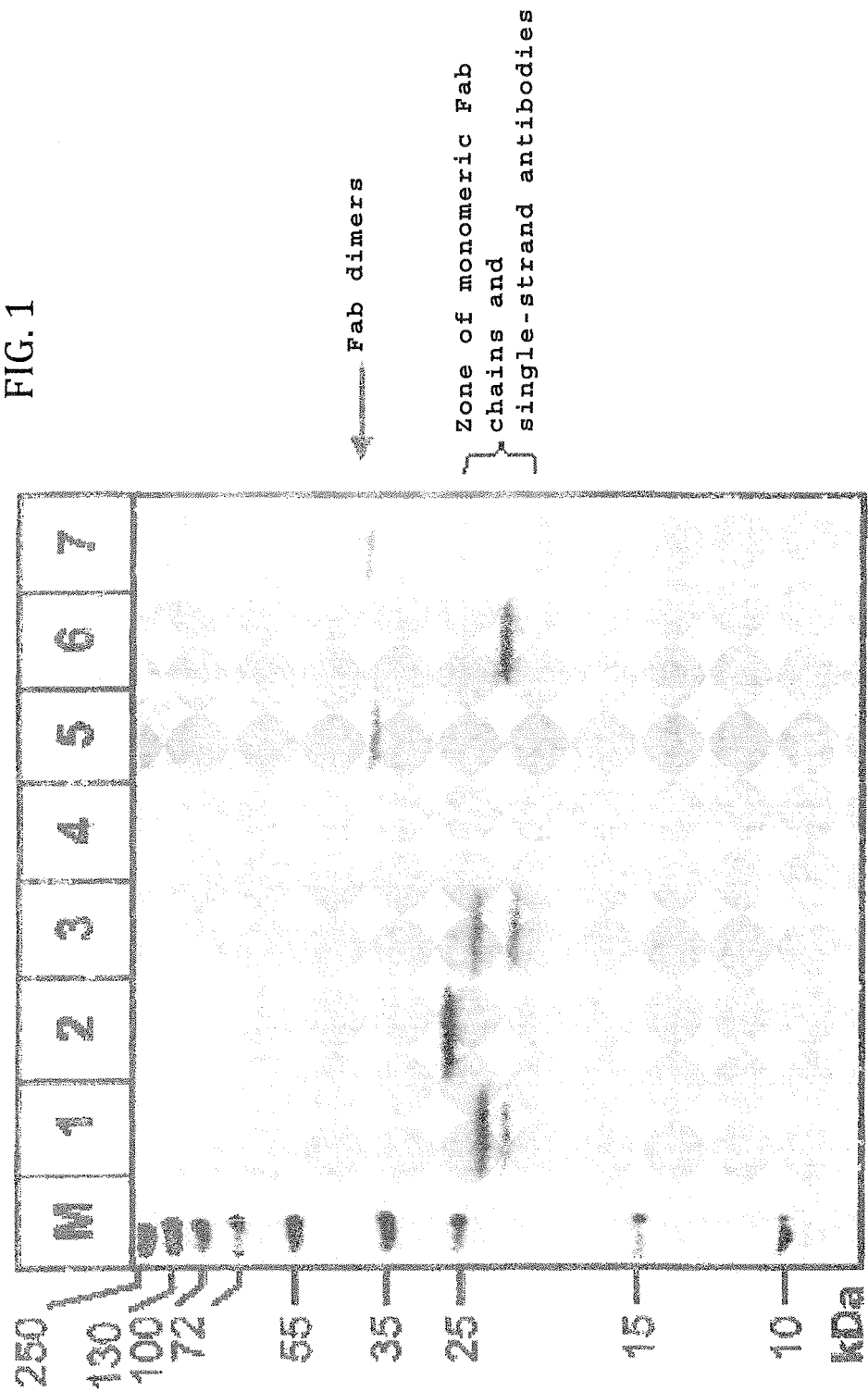
FIG. 1 shows in detail the dimerization of Fab chains by disulfide bonding.

For achieving this technical object, the invention teaches a method for producing monomeric or dimeric proteins or peptides containing internal or external disulfide bonds, comprising the following steps: a) a cell-free lysate, obtainable from eukaryotic cells, is provided, which contains functional microsomal vesicles, b) a nucleic acid coding the protein or peptide and additionally containing a signal sequence is added to the lysate, c) the lysate with the nucleic acid is held for a given time at a temperature in the range from 20 to 35° C., proteins or peptides formed with the nucleic acid being translocated into the microsomal vesicles, d) the microsomal vesicles are then dissolved, and the proteins or peptides obtained thereby are optionally separated from the lysate.

The method according to the invention differs in several aspects from prior art. Instead of the prokaryotic *E. coli* cells used up to now for the cell-free synthesis of Fab antibody fragments, eukaryotic cells are used here for the production of the expression system. Heretofore, the cell-free synthesis of Fab took place in a medium that corresponds to the cytosol of a living cell. In the invention described here, the matrices coding for antibody fragments contain signal peptide sequences. By means of these signal peptide sequences, the antibody fragments are cotranslationally translocated by natural mechanisms into microsomal vesicles, which originate from the endoplasmic reticulum. According to prior art for the cell-free protein synthesis in a system of insect cells (TNT® T7 Insect Cell Extract Protein, Promega #L1101, L1102 and EasyXpress Insect Kit II, Qiagen #32561, 32562), the protein synthesis occurs at 28 to 30° C. for one to four hours. In the system described here, the synthesis occurs at a lower incubation temperature of for instance 25° C. and an incubation time of four to five hours or less. Following the synthesis reaction, the microsomal vesicles, in which synthesized Fab is present, are dissolved by means of a detergent, and Fab is released in this way. Heretofore, pre-fabricated mRNA or circular DNA coding for Fab were used as matrices for the protein synthesis. In the method described here, linear DNA generated by PCR (polymerase chain reaction) can also be used as a matrix directly, without prior purification. The PCR-generated matrix used here can be employed as a matrix in a prokaryotic system as well as in eukaryotic systems based on insect cells (for instance *Spodoptera frugiperda*) and on mammal cells (Chinese Hamster Ovary). In the system described here the lysate used for the protein synthesis is produced from insect cells in a non-reducing medium, in contrast to prior art. The synthesis of Fab in this insect cell lysate occurs, different from prior art, not in a reducing medium, but in a defined redox medium. Different from prior art, the cell lysate preferably is not chemically pre-treated, in order to suppress activities that strongly modify the redox potential in the course of the reaction. In contrast to prior art, the system described here preferably is not supplemented with chaperones nor with protein disulfide isomerase.

Based on these differences, various advantages are achieved. The specific activity of the proteins or antibodies or antibody fragments produced according to this invention is substantially higher compared to prior art. Whereas a prokaryotic cell-free system, compared to a typical protein synthesis performance of several hundred microgram up to one milligram per milliliter reaction solution, achieves only about 30 microgram per milliliter reaction solution, and thus a very low percentage of active Fab, proteins or antibodies or antibody fragments of the invention described here are mainly produced in an active form. The consequence in prior is that for an application, where the inactive portion of the antibody fragments is disturbing, this portion has to be separated before the application by additional work steps. Such additional work steps make an automation of an antibody fragment production difficult. A disturbing effect of inactive antibody fragment may for instance be the quantification of synthesized, active antibody fragment by immunodetection (Western Blot or Enzyme Linked Immuno Sorbant Assay), since this method does normally not allow a distinction of active and inactive protein. Compared to prior art with respect to the cell-free protein synthesis system used here and based on insect cells, the advantage of the system described here is that only therein active Fab antibody fragments can be produced. The method described here permits the synthesis of antibody fragment in a completely cell-free medium, since the generation of the matrix coding for antibody fragment can also take place by the cell-free method of the PCR, in contrast to prior art. This has several advantages. The time and labor needed for the generation of the matrices and the antibody fragments is reduced from about one to two weeks to one to two days. Since for the production of antibody fragments described here, no living cells are needed in any of the steps, and no recombinant plasmid DNA needs to be produced, risks and legal limitations in dealing with genetically modified organisms do not apply. According to prior art, antibody fragments are produced in a cell-free manner up to now in systems based on *E. coli* cells. Such systems contain endotoxins. Antibody fragments produced in such systems cannot be used directly for assays based on eukaryotic cells, for instance human cells, since endotoxins normally act cytotoxically on these cells, and the measurement of the specific effect of antibody fragment on these cells is overlaid by the cytotoxic effect. In order to be able to use antibody fragments from *E. coli*-based systems in a reasonable manner in such assays, the antibody fragments must be cleaned before in additional steps. This is disadvantageous for the working time and for an automation of the production of antibody fragments. Since the system used in this invention does not contain any endotoxins, these problems do not exist here. The cell lysate of the system described here needs not be chemically pre-treated to suppress activities that would strongly modify the redox potential in the course of the reaction. Reducing chemicals need not be added to the lysate. This simplifies the handling of the system generally and particularly with regard to the automatation of the protein synthesis reaction. The system described here does not require the production and supplementation of chaperones and protein disulfide isomerase. Thus, it has a simpler structure and is more economic with respect to these components than systems according to prior art.

For the purpose of the invention, various improvements are possible. Preferably, the proteins or peptides are dimeric monoclonal antibodies or physiologically effective preferably dimeric antibody fragments. Because of the disulfide bonds within such structures, the advantages of the invention have a particularly strong effect.

Eukaryotic cells may in particular be insect cells, but HeLa cells, CHO (Chinese Hamster Ovary) cells, HEK (Human Embryonic Kidney) cells, wheat germ cells, rabbit reticulocyte cells, yeast cells (e.g. *Saccharomyces cerevisiae*), protozoa (e.g. *Leishmania*) cells or green algae may also be used. From the insect cells, for instance cells of the species *Spodoptera frugiperda*, *Drosophila melanogaster* or *Trichoplusia ni* may be used.

As signal peptides can be used in the case of the insect cells, besides melittin from honey bees, PPD1, diphosphonucleotide phosphatase/phosphodiesterase from *Lupinus luteolus*, azurocidin from *Homo sapiens* or gp67 from *Autographa californica*. Typical signal peptides for other cell species are: a) protein synthesis systems from mammal cells (e.g. HeLa, CHO, HEK, rabbit reticulocyte) the sequences from: luciferase from *Gaussia*, luciferase from *Metridia*, luciferase from *Vargula*, chymotrypsinogen from *Homo sapiens*, human Interleukin-2 from *Homo sapiens*, human Trypsinogen-2 from *Homo sapiens*, oikosin 1 from *Oikopleura dioica*, b) for protein synthesis systems from yeasts (e.g. *Saccharomyces cerevisiae*): inulinase from *Kluyveromyces marxianus*, xylanase from *Aureobasidium pullulans*, c) for protein synthesis systems from algae the sequences from: calreticulin from *Bigelowiella natans*, protein disulfide isomerase *Bigelowiella natans*, d) for protein synthesis systems from protozoa (e.g. *Leishmania*) the sequences from: gp63 from *Leishmania*, IFN-7 from *Mus musculus*. The nucleic acid to be used in the method then contains, besides the sequence coding for the protein or peptide, an additional sequence coding for the signal peptide. The latter is in most cases disposed N-terminally of the sequence coding for the protein/peptide, may however in principle also be located within it or C-terminally of it.

In step d), all conventional substances, in particular detergents may be used. Besides Brij-35, examples are: Triton X-100, NP40 (Nonidet P-40), Tween 20, CHAPS (3-[(3-cholamidopropyl)dimethylammonio]-1-propanesulfonate), DDM (n-dodecyl-beta-D-maltoside), digitonin or glucopyranoside.

Apart from that, all conventional methods and means, for instance for separating proteins or peptides from lysates, can be applied, if desired.

The invention furthermore relates to proteins or peptides or preparation containing proteins or peptides, obtainable by a method according to the invention, as well as a preparation (for instance obtained in step c) or d)) containing proteins or peptides and a cell-free lysate, obtainable from eukaryotic cells, the lysate containing functional microsomal vesicles or products of a dissolution of such microsomal vesicles, and the preparation not containing any (endogenous and/or added) chaperones and/or protein disulfide isomerases. The explanations with respect to the method apply in an analogous manner.

In the following, the invention is explained in more detail with reference to examples of execution.

Example 1

In the examples of execution, cell lysate is produced from *Spodoptera frugiperda* insect cells, as described in the document Kubick S, Schacherl J, Fleischer-Notter H, Royall E, Roberts L O, Stiege W (2003) In vitro Translation in an Insect-Based Cell-Free System. In: Swartz, J. R. (Ed.) Cell-Free Protein Expression. Springer, Berlin Heidelberg New York, 209-217, with the difference that the elution buffer used for the chromatography of the centrifugation supernatant of the cell lysate does not contain a reduction agent.

Thereafter, the lysate with a final concentration of 6.9 U S7 micrococcal nuclease (Roche) per milliliter lysate at a final concentration of 1 mM $CaCl_2$ is incubated for 20 minutes at 20° C., and the digestion is stopped by adjustment of a final concentration of 5 mM EGTA and cooling on ice. Coupled transcription/translation reactions contain 35 vol-% nuclease-treated cell lysate and further 30 mM HEPES/KOH pH 7.6, 2.9 mM magnesium acetate, 75 mM potassium acetate, 0.25 mM spermidine, 20 mg/ml creatine phosphate, 1.75 mM ATP, 0.3 mM CTP, 0.3 mM GTP, 0.3 mM UTP, 0.33 mM P1,P3-di-(guanosine-5')-triphosphate, 2.5 mM glutathione in oxidized form, 0.5 mM glutathione in reduced form, 100 U/ml ribonuclease inhibitor RNasin (Promega), 50 U/μl T7 RNA polymerase (Roche), 17.5 μg/ml tRNA from baker's yeast (Roche), 0.1 mM each of all 20 natural amino acids, 0.1 mg/ml creatine kinase (Roche) and respectively 7.5 μg/ml plasmid DNA coding for light and heavy chain of a Fab antibody fragment. As needed, L-[U-14C]leucine (GE Healthcare) is added to the reaction for adjusting a molar activity of 40 dpm/pmol. The reaction batches are incubated for 4 hours at 25° C. under agitation at 700 rpm in the thermomixer (Eppendorf).

Following the synthesis reaction, the reaction batch is reacted for the lysis of the microsomal vesicles containing Fab with Brij-35 solution in a final concentration of 0.05% and incubated for 5 min at room temperature.

Example 2

Anti-hen egg white lysozyme Fab antibody fragment and anti-human CD4 Fab antibody fragment are synthesized as described in Example 1. As matrices are used the plasmid pIX5.0-Mel-LaLys and pIX5.0-HaLys (anti-lysozyme) and the linear DNA matrices Mel-VLCL-SII and Mel-VHCH1 (anti-CD4) generated with the EasyXpress Linear Template Kit plus (Qiagen), which code according to the invention described here for a signal peptide at the N-terminus of the Fab chains.

After the reaction, two 5 μl aliquots of each synthesis reaction were precipitated with acetone. Of the respectively two resulting pellets, one was dissolved in SDS sample buffer with reduction agent, and disulfide bonds were cleaved by heating to 90° C. for 3 minutes. The respectively second pellet was dissolved in SDS sample buffer without reduction agent by incubation for 30 minutes at 37° C., without cleaving the generated disulfide bonds. FIG. 1 shows the result of the analysis as an autoradiograph after SDS PAGE.

According thereto, in the autoradiograph with the samples treated with reduction agent, the co-expressed light and heavy chains can be seen as bands with the expected molecular weight, whereas under non-reducing conditions, bands are detected having a molecular weight as it is expected for Fab dimer. The monomeric chains were reacted in the protein synthesis system mainly to dimers.

FIG. 1 shows in detail the dimerization of Fab chains by disulfide bonding. Anti-hen egg white lysozyme Fab antibody fragment and anti-human CD4 Fab antibody fragment were synthesized in a cell-free manner according to the invention described here and the linkage of the individual light and heavy immunoglobulin chains to the disulfide-bonded dimer was analyzed by gel electrophoresis. Tracks 1-3: The disulfide bonds of the Fab chains in the reaction batches were cleaved by heating in reduction agent-containing sample buffer. Tracks 5-7: The disulfide bonds of the Fab chains in the reaction batches were maintained by treating in sample buffer without reduction agent. Tracks 1 and 5: co-expression of light and heavy chain of anti-hen egg white lysozyme Fab antibody fragment, Tracks 2 and 6: control batch with anti-lysozyme single-stranded antibody without signal peptide synthesized in presence of 0.5 μM protein disulfide isomerase (Takara), Tracks 3 and 7: co-expression of light and heavy chain of anti-human CD4 Fab antibody fragment, Track 4: empty.

Example 3

Figure 2:
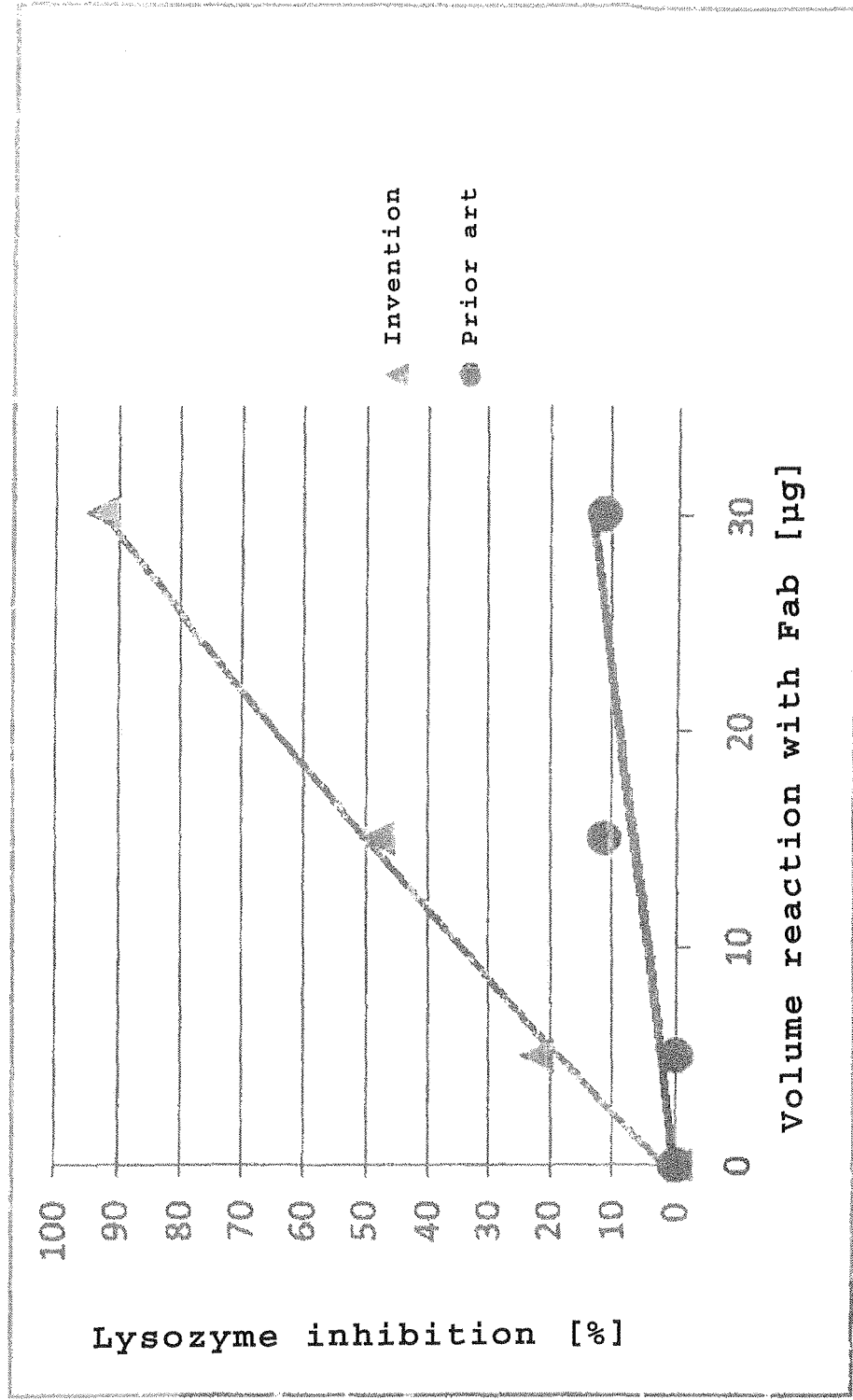
FIG. 2 shows the result of the comparison of tests of anti-hen egg white lysozyme Fab antibody fragment according to the invention versus anti-hen egg white lysozyme Fab antibody fragment according to prior art.

An anti-hen egg white lysozyme Fab antibody fragment is synthesized as described in Example 1. As matrices are used the plasmid pIX5.0-Mel-LaLys and pIX5.0-HaLys coding according to the invention described here for a signal peptide at the N-terminus of the Fab chains. The plasmids used for carrying out prior art, coding for the same proteins as the pIX5.0 plasmid variants, not having however a sequence coding for signal peptide, are pIX3.0-LaLys and pIX3.0a-HaLys. For the determination of the Fab activity, hen egg white lysozyme (Sigma-Aldrich) with a specific activity of 56,400 U/mg is incubated with an aliquot of the reaction batch with the synthesized Fab and parallelly with an aliquot from a control batch, and the specific inhibition of the lysozyme-dependent lysis of *Micrococcus lysodeicticus* cells is determined as described in the document Merk H, Stiege W, Tsumoto K, Kumagai I, Erdmann V A (1999) Cell-free Expression of two Single-Chain Monoclonal Antibodies against Lysozyme: Effect of Domain Arrangement on the Expression. J Biochem 125:328-333. By way of comparison, anti-hen egg white lysozyme Fab antibody fragment according to prior art is parallelly synthesized with the EasyXpress Insect Kit II (Qiagen) according to manufacturer's instructions and is also used for the determination of the activity. The result of the comparison tests is shown in FIG. 2. Anti-hen egg white lysozyme Fab antibody fragment was synthesized in a cell-free manner a) according to prior art and b) according to the invention described here. 5, 15 and 30 μl reaction batch each with synthesized anti-hen egg white lysozyme Fab antibody fragment from the different synthesis methods and 30 μl control reaction batch with synthesized erythropoietin were incubated with 20 ng hen egg white lysozyme, and the specific inhibition of lysozyme was detected. The values for unspecific inhibition due to the effect of the respective control reaction batch were deducted from the measurement values.

Fab that is synthesized according to the method described here has an activity being an order of magnitude higher compared to a prior art batch.

Example 4

An anti-hen egg white lysozyme Fab antibody fragment is synthesized as described in Example 1, with the difference that before the synthesis reaction, microsomal vesicles originating from the endoplasmic reticulum were to a large extent removed from the nuclease-treated lysate. For this purpose, the lysate is centrifuged for 20 minutes at 16,000×g and 4° C. The centrifugation supernatant of the nuclease-treated lysate liberated from the pelletized vesicles is then used for the synthesis reaction of Fab. In parallel, the synthesis of Fab is carried out according to the invention with lysate containing vesicles as described in Example 2. The yield and activity of the synthesized proteins are shown in FIGS. 3 and 4.

Figure 3:
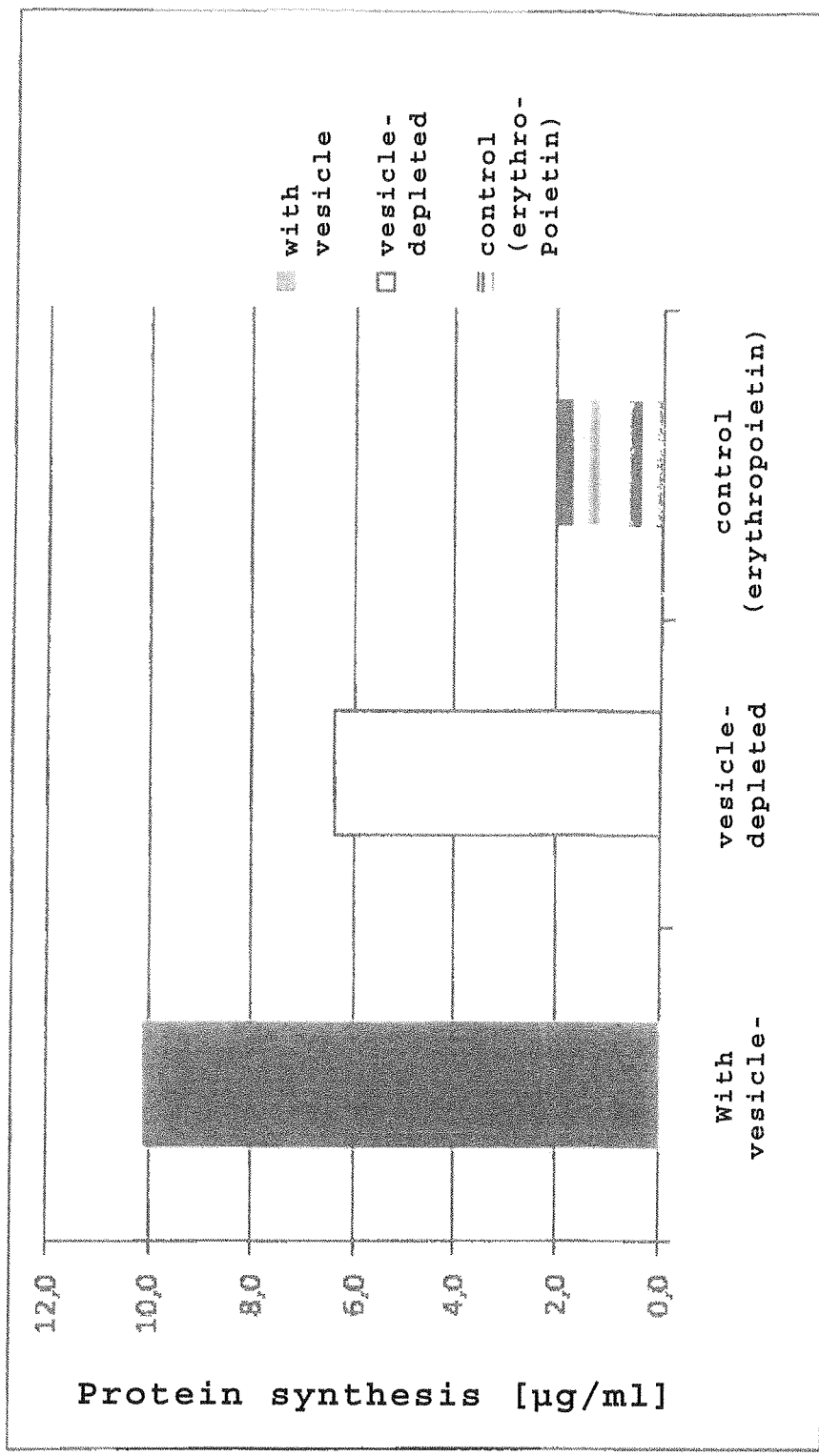
FIG. 3 shows the determination of the synthesis yield of Fab synthesized according to the invention and in comparison with vesicle-depleted lysate.
Figure 4:
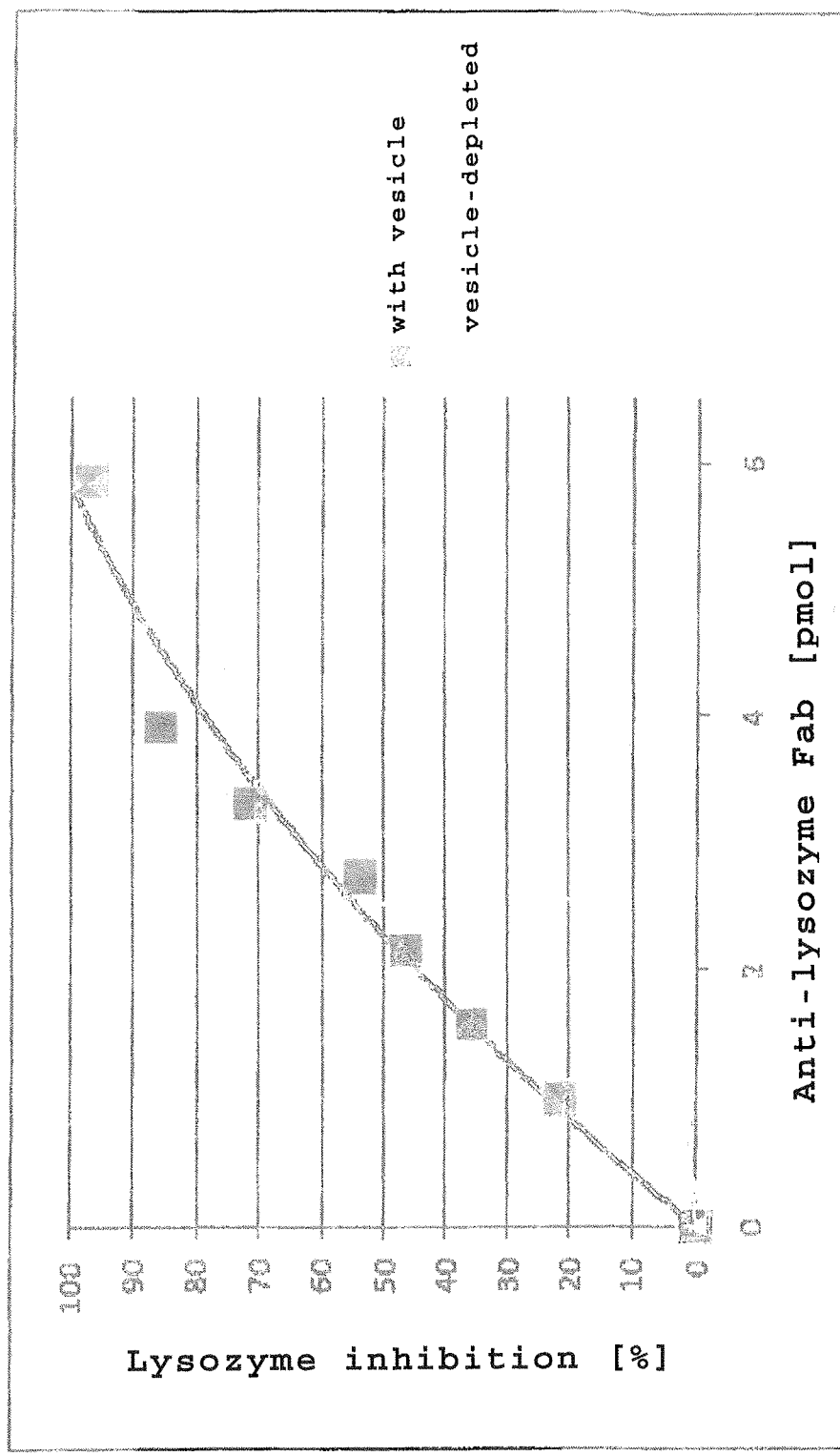
FIG. 4 shows the determination of activity of Fab synthesized according to the invention and with vesicle-depleted lysate.

FIG. 3 shows the determination of the synthesis yield of Fab synthesized according to the invention and in comparison with vesicle-depleted lysate. The yields of the newly synthesized, radioactively marked proteins were determined by scintillation measurement of the material insoluble in hot trichloroacetic acid in 5 μl aliquots of the reaction batches. FIG. 4 shows the determination of activity of Fab synthesized according to the invention and with vesicle-depleted lysate. The activity of anti-hen egg white lysozyme Fab antibody fragment was determined analogously to Example 3. There is shown the respective extent of the lysozyme inhibition as a function of the employed Fab quantity, which was determined according to FIG. 3 by a radioactivity measurement.

Fab that is synthesized according to the method described here has an activity being approx. one order of magnitude higher compared to a batch that does not include the translocation of Fab in microsomal vesicles and thus represents part only of the method of this invention.

Example 5

In the following, the vector maps and sequences of the DNA matrices used for the cell-free protein synthesis are shown and described.

Figure 5:
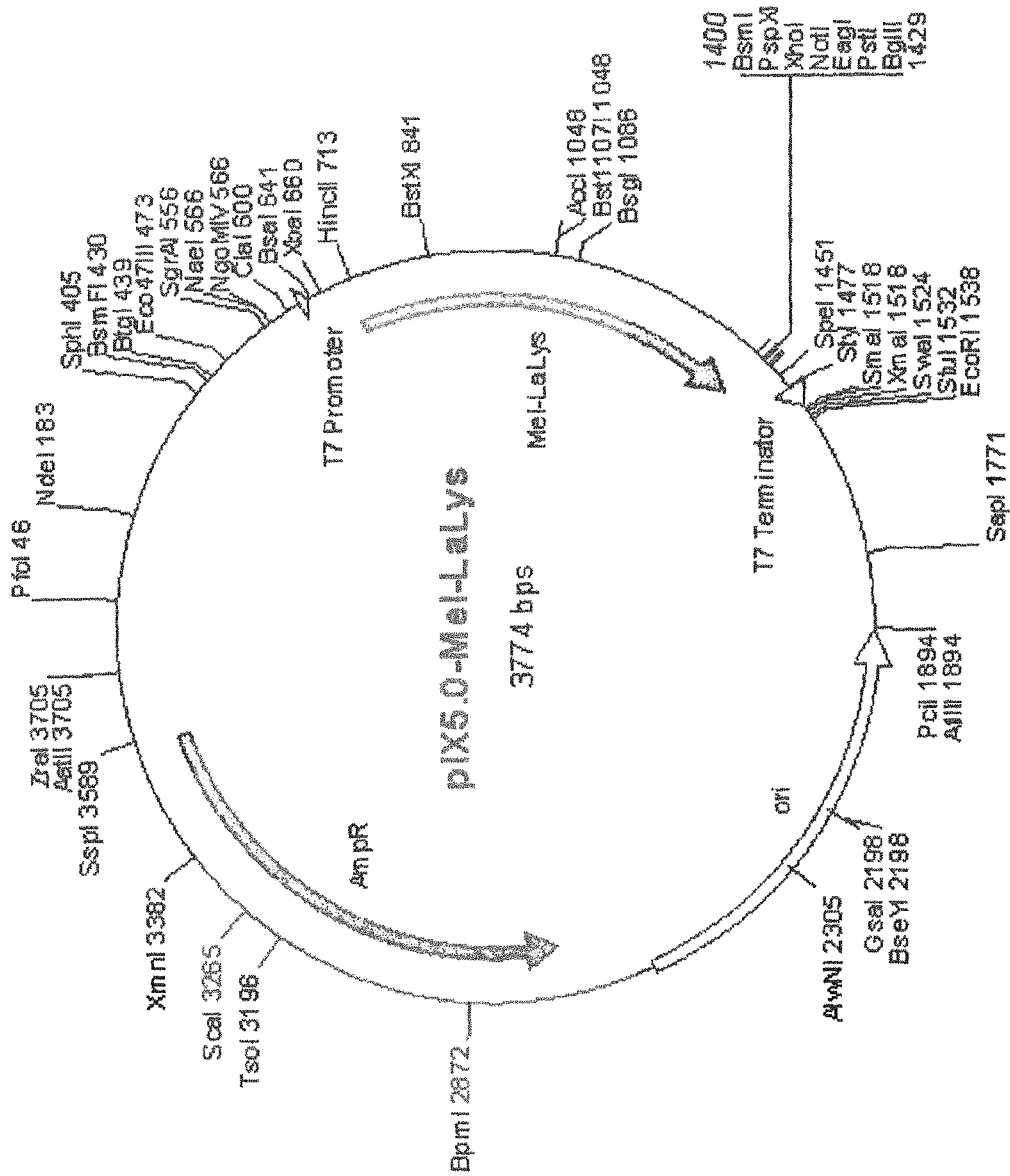
FIG. 5 shows the plasmid pIX5.0-Mel-LaLys (plasmid DNA) having SEQ.ID.NO: 1.

FIG. 5 shows the plasmid pIX5.0-Mel-LaLys (plasmid DNA) with the following sequence details:

| Type | Start | End | Name |
|---|---|---|---|
| Region | 622 | 638 | T7 transcription promoter |
| Gene | 701 | 1408 | Mel-LaLys, light chain anti-lysozyme Fab with melittin signal peptide |
| Region | 1475 | 1513 | T7 transcription terminator |
| Region | 2569 | 1896 | complementary, replication origin (ori) |
| Gene | 3574 | 2714 | complementary, ampicillin resistance gene (β-lactamase) |

(SEQ. ID. NO: 1)
TCGCGCGTTTCGGTGATGACGGTGAAAACCTCTGACACATGCAGCT
CCCGGAGACGGTCACAGCTTGTCTGTAAGCGGATGCCGGGAGCAG
ACAAGCCCGTCAGGGCGCGTCAGCGGGTGTTGGCGGGTGTCGGGG
CTGGCTTAACTATGCGGCATCAGAGCAGATTGTACTGAGAGTGCAC
CATATGCGGTGTGAAATACCGCACAGATGCGTAAGGAGAAAATAC
CGCATCAGGCGCCATTCGCCATTCAGGCTGCGCAACTGTTGGGAAG
GGCGATCGGTGCGGGCCTCTTCGCTATTACGCCAGCTGGCGAAAGG
GGGATGTGCTGCAAGGCGATTAAGTTGGGTAACGCCAGGGTTTTCC
CAGTCACGACGTTGTAAAACGACGGCCAGTGCCAAGCTTGCATGC
AAGGAGATGGCGCCCAACAGTCCCCCGGCCACGGGGCCTGCCACC
ATACCCACGCCGAAACAAGCGCTCATGAGCCCGAAGTGGCGAGCC
CGATCTTCCCCATCGGTGATGTCGGCGATATAGGCGCCAGCAACCG
CACCTGTGGCGCCGGTGATGCCGGCCACGATGCGTCCGGCGTAGA
GGATCGAGATCGATCTCGATCCCGCGAAATTAATACGACTCACTAT
AGGGAGACCACAACGGTTTCCCTCTAGAAATAATTTTGTTTAACTT
TAAGAAGGAGATATACCATGAAATTCTTAGTCAACGTTGCCCTGGT
TTTTATGGTGGTGTATATTAGCTATATTTATGCCGATATTGTGCTGA
CCCAGAGTCCGGCAACCCTGAGCGTTACACCGGGTAATAGCGTTAG
CCTGAGCTGTCGTGCAAGCCAGAGCATTGGTAATAATCTGCATTGG
TATCAGCAGAAAAGCCATGAAAGTCCGCGTCTGCTGATTAAATATG
CAAGCCAGTCAATTAGCGGTATTCCGAGCCGTTTTAGCGGTAGCGG
TAGTGGCACCGATTTTACCCTGAGCATTAATAGCGTTGAAACCGAA
GATTTTGGCATGTATTTTTGCCAGCAGAGCAATAGCTGGCCGTATA
CCTTTGGTGGTGGCACCAAACTGGAAATTAAACGTGCAGATGCAGC

ACCGACCGTTAGCATTTTTCCGCCGAGCAGCGAACAGCTGACCAGC
GGTGGTGCAAGCGTTGTTTGTTTTCTGAATAACTTTTATCCGAAAG
ATATCAATGTGAAATGGAAAATTGATGGCAGCGAACGTCAGAATG
GTGTTCTGAATAGCTGGACCGATCAGGATAGCAAAGATAGCACCT
ATAGCATGAGCAGCACCCTGACCCTGACCAAAGATGAATATGAAC
GCCATAATAGCTATACCTGTGAAGCAACCCATAAAACCAGCACCA
GCCCGATTGTTAAAAGCTTTAATCGCAATGAATGCTAATAACTCGA
GCGGCCGCCTGCAGATCTAAATAATAAGTAATTAACTAGTGAGCA
ATAACTAGCATAACCCCTTGGGGCCTCTAAACGGGTCTTGAGGGGT
TTTTTGATATCCCGGGATTTAAATAGGCCTGAATTCGTAATCATGG
TCATAGCTGTTTCCTGTGTGAAATTGTTATCCGCTCACAATTCCACA
CAACATACGAGCCGGAAGCATAAAGTGTAAAGCCTGGGGTGCCTA
ATGAGTGAGCTAACTCACATTAATTGCGTTGCGCTCACTGCCCGCT
TTCCAGTCGGGAAACCTGTCGTGCCAGCTGCATTAATGAATCGGCC
AACGCGCGGGAGAGGCGGTTTGCGTATTGGGCGCTCTTCCGCTTC
CTCGCTCACTGACTCGCTGCGCTCGGTCGTTCGGCTGCGGCGAGCG
GTATCAGCTCACTCAAAGGCGGTAATACGGTTATCCACAGAATCAG
GGGATAACGCAGGAAAGAACATGTGAGCAAAAGGCCAGCAAAAG
GCCAGGAACCGTAAAAAGGCCGCGTTGCTGGCGTTTTTCCATAGGC
TCCGCCCCCCTGACGAGCATCACAAAAATCGACGCTCAAGTCAGA
GGTGGCGAAACCCGACAGGACTATAAAGATACCAGGCGTTTCCCC
CTGGAAGCTCCCTCGTGCGCTCTCCTGTTCCGACCCTGCCGCTTACC
GGATACCTGTCCGCCTTTCTCCCTTCGGGAAGCGTGGCGCTTTCTC
ATAGCTCACGCTGTAGGTATCTCAGTTCGGTGTAGGTCGTTCGCTC
CAAGCTGGGCTGTGTGCACGAACCCCCCGTTCAGCCCGACCGCTGC
GCCTTATCCGGTAACTATCGTCTTGAGTCCAACCCGGTAAGACACG
ACTTATCGCCACTGGCAGCAGCCACTGGTAACAGGATTAGCAGAG
CGAGGTATGTAGGCGGTGCTACAGAGTTCTTGAAGTGGTGGCCTAA
CTACGGCTACACTAGAAGGACAGTATTTGGTATCTGCGCTCTGCTG
AAGCCAGTTACCTTCGGAAAAAGAGTTGGTAGCTCTTGATCCGGCA
AACAAACCACCGCTGGTAGCGGTGGTTTTTTTGTTTGCAAGCAGCA
GATTACGCGCAGAAAAAAAGGATCTCAAGAAGATCCTTTGATCTTT
TCTACGGGGTCTGACGCTCAGTGGAACGAAAACTCACGTTAAGGG
ATTTTGGTCATGAGATTATCAAAAAGGATCTTCACCTAGATCCTTT
TAAATTAAAAATGAAGTTTTAAATCAATCTAAAGTATATATGAGTA
AACTTGGTCTGACAGTTACCAATGCTTAATCAGTGAGGCACCTATC
TCAGCGATCTGTCTATTTCGTTCATCCATAGTTGCCTGACTCCCCGT
CGTGTAGATAACTACGATACGGGAGGGCTTACCATCTGGCCCCAGT
GCTGCAATGATACCGCGAGATCCACGCTCACCGGCTCCAGATTTAT
CAGCAATAAACCAGCCAGCCGGAAGGGCCGAGCGCAGAAGTGGTC

CTGCAACTTTATCCGCCTCCATCCAGTCTATTAATTGTTGCCGGGA

AGCTAGAGTAAGTAGTTCGCCAGTTAATAGTTTGCGCAACGTTGTT

GCCATTGCTACAGGCATCGTGGTGTCACGCTCGTCGTTTGGTATGG

CTTCATTCAGCTCCGGTTCCCAACGATCAAGGCGAGTTACATGATC

CCCCATGTTGTGCAAAAAAGCGGTTAGCTCCTTCGGTCCTCCGATC

GTTGTCAGAAGTAAGTTGGCCGCAGTGTTATCACTCATGGTTATGG

CAGCACTGCATAATTCTCTTACTGTCATGCCATCCGTAAGATGCTTT

TCTGTGACTGGTGAGTACTCAACCAAGTCATTCTGAGAATAGTGTA

TGCGGCGACCGAGTTGCTCTTGCCCGGCGTCAATACGGGATAATAC

CGCGCCACATAGCAGAACTTTAAAAGTGCTCATCATTGGAAAACGT

TCTTCGGGGCGAAAACTCTCAAGGATCTTACCGCTGTTGAGATCCA

GTTCGATGTAACCCACTCGTGCACCCAACTGATCTTCAGCATCTTTT

ACTTTCACCAGCGTTTCTGGGTGAGCAAAAACAGGAAGGCAAAAT

GCCGCAAAAAAGGGAATAAGGGCGACACGGAAATGTTGAATACTC

ATACTCTTCCTTTTTCAATATTATTGAAGCATTTATCAGGGTTATTG

TCTCATGAGCGGATACATATTTGAATGTATTTAGAAAAATAAACAA

ATAGGGGTTCCGCGCACATTTCCCCGAAAAGTGCCACCTGACGTCT

AAGAAACCATTATTATCATGACATTAACCTATAAAAATAGGCGTAT

CACGAGGCCCTTTCGTC

Figure 6:
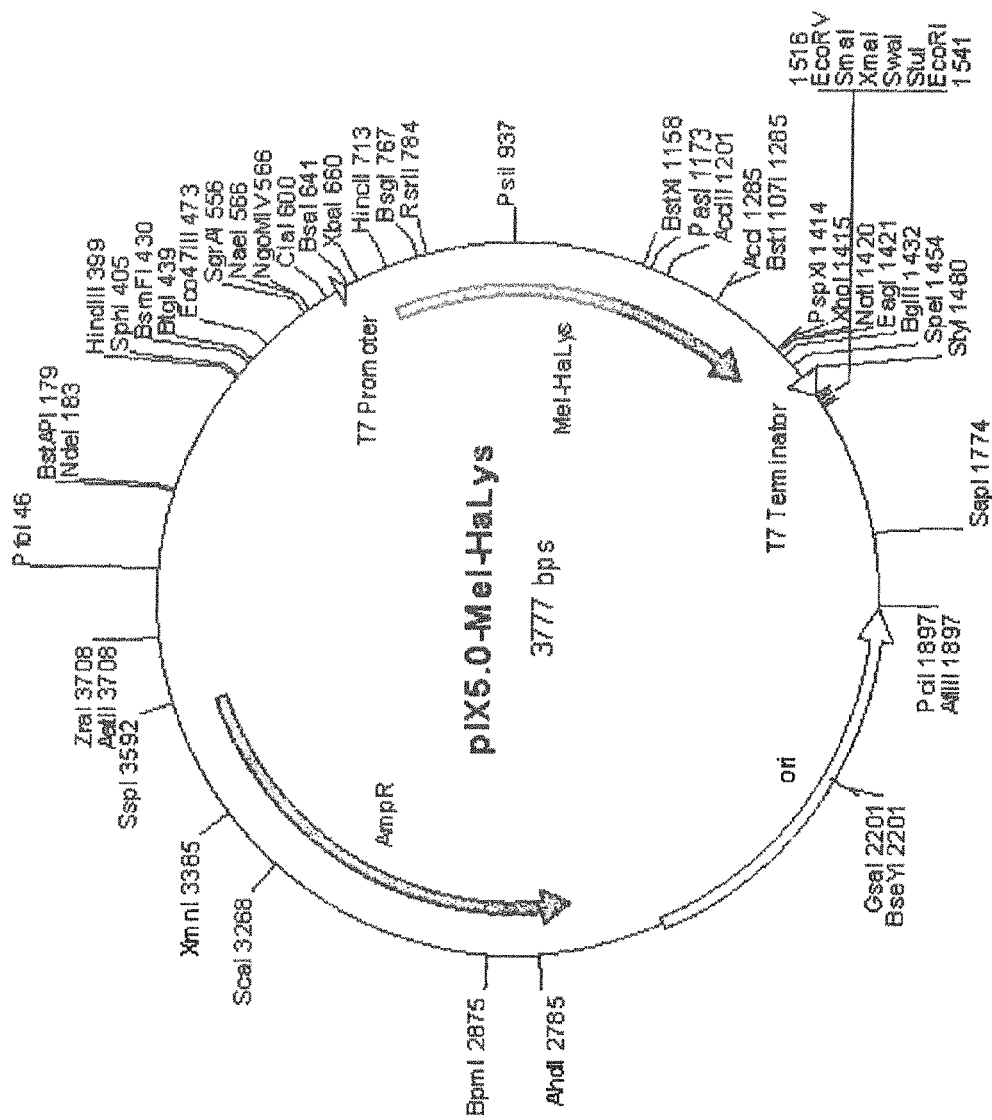
FIG. 6 shows the plasmid pIX5.0-Mel-HaLys (plasmid DNA) having SEQ.ID.NO: 2.

FIG. 6 shows the plasmid pIX5.0-Mel-HaLys (plasmid DNA) with the following sequence details:

| Type   | Start | End  | Name |
|--------|-------|------|------|
| Region | 622   | 638  | T7 transcription promoter |
| Gene   | 701   | 1411 | Mel-HaLys, light chain anti-lysozyme Fab with melittin signal peptide |
| Region | 1478  | 1516 | T7 transcription terminator |
| Region | 2572  | 1899 | complementary, replication origin (ori) |
| Gene   | 3577  | 2717 | complementary, ampicillin resistance gene (β-lactamase) |

(SEQ. ID. NO: 2)
TCGCGCGTTTCGGTGATGACGGTGAAAACCTCTGACACATGCAGCT

CCCGGAGACGGTCACAGCTTGTCTGTAAGCGGATGCCGGGAGCAG

ACAAGCCCGTCAGGGCGCGTCAGCGGGTGTTGGCGGGTGTCGGGG

CTGGCTTAACTATGCGGCATCAGAGCAGATTGTACTGAGAGTGCAC

CATATGCGGTGTGAAATACCGCACAGATGCGTAAGGAGAAAATAC

CGCATCAGGCGCCATTCGCCATTCAGGCTGCGCAACTGTTGGGAAG

GGCGATCGGTGCGGGCCTCTTCGCTATTACGCCAGCTGGCGAAAGG

GGGATGTGCTGCAAGGCGATTAAGTTGGGTAACGCCAGGGTTTTCC

CAGTCACGACGTTGTAAAACGACGGCCAGTGCCAAGCTTGCATGC

AAGGAGATGGCGCCCAACAGTCCCCCGGCCACGGGGCCTGCCACC

ATACCCACGCCGAAACAAGCGCTCATGAGCCCGAAGTGGCGAGCC

CGATCTTCCCCATCGGTGATGTCGGCGATATAGGCGCCAGCAACCG

CACCTGTGGCGCCGGTGATGCCGGCCACGATGCGTCCGGCGTAGA

GGATCGAGATCGATCTCGATCCCGCGAAATTAATACGACTCACTAT

AGGGAGACCACAACGGTTTCCCTCTAGAAATAATTTTGTTTAACTT

TAAGAAGGAGATATACCATGAAATTCTTAGTCAACGTTGCCCTGGT

TTTTATGGTGGTGTATATTAGCTATATTTATGCCGATGTGCAGCTGC

AGGAAAGCGGTCCGAGCCTGGTTAAACCGAGCCAGACCCTGAGCC

TGACCTGTAGCGTTACCGGTGATAGCATTACCAGCGATTATTGGAG

CTGGATTCGTAAATTTCCGGGTAATCGTCTGGAATATATGGGTTAT

GTTAGCTATAGCGGCAGCACCTATTATAATCCGAGCCTGAAAAGCC

GTATTAGCATTACCCGTGATACCAGCAAAAATCAGTATTATCTGGA

TCTGAATAGCGTGACCACCGAAGATACCGCAACCTATTACTGTGCA

AATTGGGATGGTGATTATTGGGGTCAGGGCACCCTGGTTACCGTTA

GCGCAGCAAAAACCACACCGCCGAGCGTTTATCCGCTGGCACCGG

GTAGCGCAGCACAGACCAATAGCATGGTTACCCTGGGTTGTCTGGT

GAAAGGTTATTTTCCGGAACCGGTTACCGTTACCTGGAATAGCGGT

AGCCTGAGCAGCGGTGTTCATACCTTTCCGGCAGTTCTGCAGAGCG

ATCTGTATACCCTGAGCAGCAGCGTTACCGTTCCGAGCAGTCCGCG

TCCGAGCGAAACCGTTACCTGTAATGTTGCACATCCGGCAAGCAGC

ACCAAAGTTGATAAAAAAATTGTTCCGCGTGATTGCTAATAACTCG

AGCGGCCGCCTGCAGATCTAAATAATAAGTAATTAACTAGTGAGC

AATAACTAGCATAACCCCTTGGGGCCTCTAAACGGGTCTTGAGGGG

TTTTTTGATATCCCGGGATTTAAATAGGCCTGAATTCGTAATCATG

GTCATAGCTGTTTCCTGTGTGAAATTGTTATCCGCTCACAATTCCAC

ACAACATACGAGCCGGAAGCATAAAGTGTAAAGCCTGGGGTGCCT

AATGAGTGAGCTAACTCACATTAATTGCGTTGCGCTCACTGCCCGC

TTTCCAGTCGGGAAACCTGTCGTGCCAGCTGCATTAATGAATCGGC

CAACGCGCGGGGAGAGGCGGTTTGCGTATTGGGCGCTCTTCCGCTT

CCTCGCTCACTGACTCGCTGCGCTCGGTCGTTCGGCTGCGGCGAGC

GGTATCAGCTCACTCAAAGGCGGTAATACGGTTATCCACAGAATCA

GGGGATAACGCAGGAAAGAACATGTGAGCAAAAGGCCAGCAAAA

GGCCAGGAACCGTAAAAAGGCCGCGTTGCTGGCGTTTTTCCATAGG

CTCCGCCCCCCTGACGAGCATCACAAAAATCGACGCTCAAGTCAG

AGGTGGCGAAACCCGACAGGACTATAAAGATACCAGGCGTTTCCC

CCTGGAAGCTCCCTCGTGCGCTCTCCTGTTCCGACCCTGCCGCTTAC

-continued

CGGATACCTGTCCGCCTTTCTCCCTTCGGGAAGCGTGGCGCTTTCTC

ATAGCTCACGCTGTAGGTATCTCAGTTCGGTGTAGGTCGTTCGCTC

CAAGCTGGGCTGTGTGCACGAACCCCCCGTTCAGCCCGACCGCTGC

GCCTTATCCGGTAACTATCGTCTTGAGTCCAACCCGGTAAGACACG

ACTTATCGCCACTGGCAGCAGCCACTGGTAACAGGATTAGCAGAG

CGAGGTATGTAGGCGGTGCTACAGAGTTCTTGAAGTGGTGGCCTAA

CTACGGCTACACTAGAAGGACAGTATTTGGTATCTGCGCTCTGCTG

AAGCCAGTTACCTTCGGAAAAAGAGTTGGTAGCTCTTGATCCGGCA

AACAAACCACCGCTGGTAGCGGTGGTTTTTTTGTTTGCAAGCAGCA

GATTACGCGCAGAAAAAAAGGATCTCAAGAAGATCCTTTGATCTTT

TCTACGGGGTCTGACGCTCAGTGGAACGAAAACTCACGTTAAGGG

ATTTTGGTCATGAGATTATCAAAAAGGATCTTCACCTAGATCCTTT

TAAATTAAAAATGAAGTTTTAAATCAATCTAAAGTATATATGAGTA

AACTTGGTCTGACAGTTACCAATGCTTAATCAGTGAGGCACCTATC

TCAGCGATCTGTCTATTTCGTTCATCCATAGTTGCCTGACTCCCCGT

CGTGTAGATAACTACGATACGGGAGGGCTTACCATCTGGCCCCAGT

GCTGCAATGATACCGCGAGATCCACGCTCACCGGCTCCAGATTTAT

CAGCAATAAACCAGCCAGCCGGAAGGGCCGAGCGCAGAAGTGGTC

CTGCAACTTTATCCGCCTCCATCCAGTCTATTAATTGTTGCCGGGA

AGCTAGAGTAAGTAGTTCGCCAGTTAATAGTTTGCGCAACGTTGTT

GCCATTGCTACAGGCATCGTGGTGTCACGCTCGTCGTTTGGTATGG

CTTCATTCAGCTCCGGTTCCCAACGATCAAGGCGAGTTACATGATC

CCCCATGTTGTGCAAAAAAGCGGTTAGCTCCTTCGGTCCTCCGATC

GTTGTCAGAAGTAAGTTGGCCGCAGTGTTATCACTCATGGTTATGG

CAGCACTGCATAATTCTCTTACTGTCATGCCATCCGTAAGATGCTTT

TCTGTGACTGGTGAGTACTCAACCAAGTCATTCTGAGAATAGTGTA

TGCGGCGACCGAGTTGCTCTTGCCCGGCGTCAATACGGGATAATAC

CGCGCCACATAGCAGAACTTTAAAAGTGCTCATCATTGGAAAACGT

TCTTCGGGGCGAAAACTCTCAAGGATCTTACCGCTGTTGAGATCCA

GTTCGATGTAACCCACTCGTGCACCCAACTGATCTTCAGCATCTTTT

ACTTTCACCAGCGTTTCTGGGTGAGCAAAAACAGGAAGGCAAAAT

GCCGCAAAAAAGGGAATAAGGGCGACACGGAAATGTTGAATACTC

ATACTCTTCCTTTTTCAATATTATTGAAGCATTTATCAGGGTTATTG

TCTCATGAGCGGATACATATTTGAATGTATTTAGAAAAATAAACAA

ATAGGGGTTCCGCGCACATTTCCCCGAAAAGTGCCACCTGACGTCT

AAGAAACCATTATTATCATGACATTAACCTATAAAAATAGGCGTAT

CACGAGGCCCTTTCGTC

Figure 7:
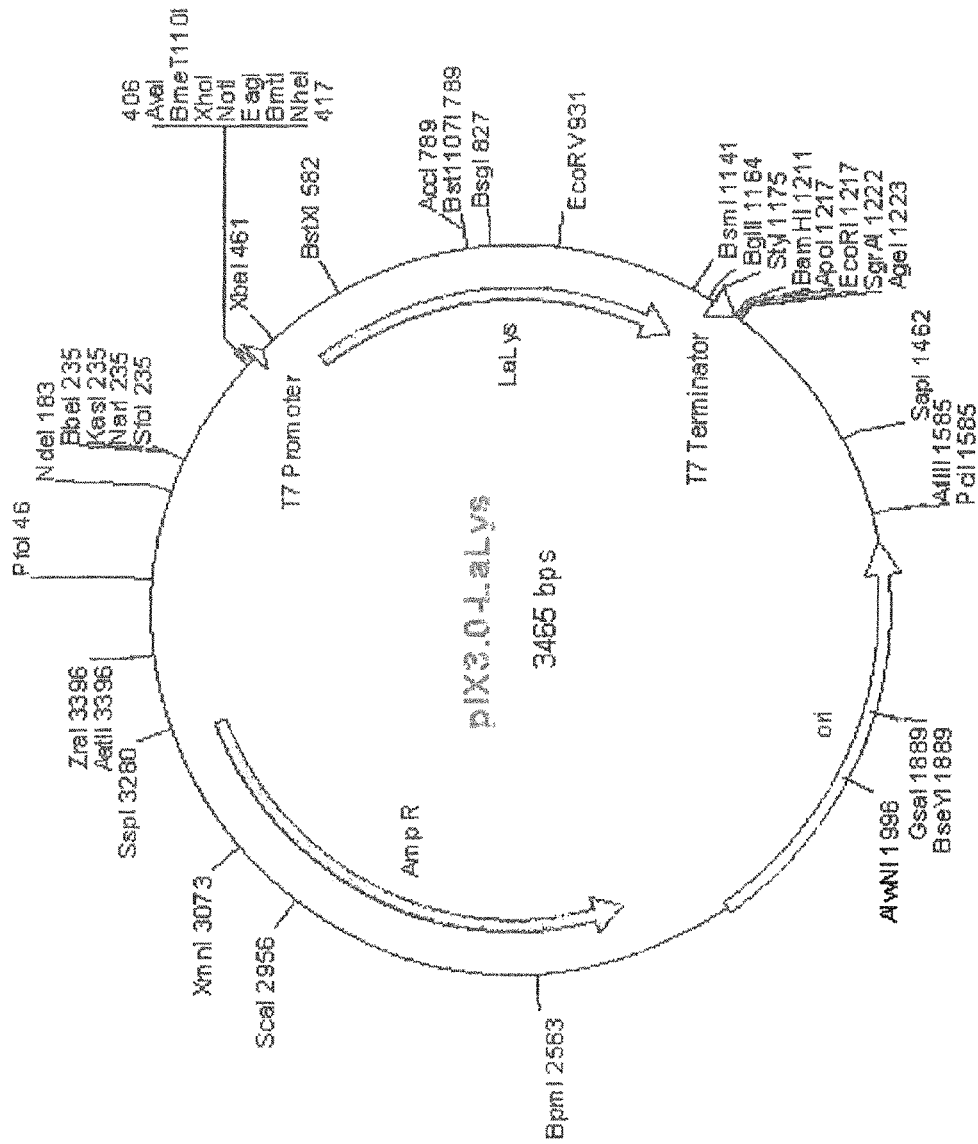
FIG. 7 shows the plasmid pIX3.0-LaLys (plasmid DNA) having SEQ.ID.NO: 3.

FIG. 7 shows the plasmid pIX3.0-LaLys (plasmid DNA) with the following sequence details:

| Type   | Start | End  | Name                                               |
|--------|-------|------|----------------------------------------------------|
| Region | 423   | 439  | T7 transcription promoter                          |
| Gene   | 502   | 1149 | HaLys, light chain anti-lysozyme Fab               |
| Region | 1173  | 1211 | T7 transcription terminator                        |
| Region | 2260  | 1627 | complementary, replication origin (ori)            |
| Gene   | 3265  | 2405 | complementary, ampicillin resistance gene (β-lactamase) |

(SEQ. ID. NO: 3)
TCGCGCGTTTCGGTGATGACGGTGAAAACCTCTGACACATGCAGCT

CCCGGAGACGGTCACAGCTTGTCTGTAAGCGGATGCCGGGAGCAG

ACAAGCCCGTCAGGGCGCGTCAGCGGGTGTTGGCGGGTGTCGGGG

CTGGCTTAACTATGCGGCATCAGAGCAGATTGTACTGAGAGTGCAC

CATATGCGGTGTGAAATACCGCACAGATGCGTAAGGAGAAAATAC

CGCATCAGGCGCCATTCGCCATTCAGGCTGCGCAACTGTTGGGAAG

GGCGATCGGTGCGGGCCTCTTCGCTATTACGCCAGCTGGCGAAAGG

GGGATGTGCTGCAAGGCGATTAAGTTGGGTAACGCCAGGGTTTTCC

CAGTCACGACGTTGTAAAACGACGGCCAGTGCCAAGCTTTCTCGAG

CGGCCGCTAGCTAATACGACTCACTATAGGGAGACCACAACGGTTT

CCCTCTAGAAATAATTTTGTTTAACTTTAAGAAGGAGATAAACAAT

GGATATTGTGCTGACCCAGAGTCCGGCAACCCTGAGCGTTACACCG

GGTAATAGCGTTAGCCTGAGCTGTCGTGCAAGCCAGAGCATTGGTA

ATAATCTGCATTGGTATCAGCAGAAAAGCCATGAAAGTCCGCGTCT

GCTGATTAAATATGCAAGCCAGTCAATTAGCGGTATTCCGAGCCGT

TTTAGCGGTAGCGGTAGTGGCACCGATTTTACCCTGAGCATTAATA

GCGTTGAAACCGAAGATTTTGGCATGTATTTTTGCCAGCAGAGCAA

TAGCTGGCCGTATACCTTTGGTGGTGGCACCAAACTGGAAATTAAA

CGTGCAGATGCAGCACCGACCGTTAGCATTTTTCCGCCGAGCAGCG

AACAGCTGACCAGCGGTGGTGCAAGCGTTGTTTGTTTTCTGAATAA

CTTTTATCCGAAAGATATCAATGTGAAATGGAAAATTGATGGCAGC

GAACGTCAGAATGGTGTTCTGAATAGCTGGACCGATCAGGATAGC

AAAGATAGCACCTATAGCATGAGCAGCACCCTGACCCTGACCAAA

GATGAATATGAACGCCATAATAGCTATACCTGTGAAGCAACCCATA

AAACCAGCACCAGCCCGATTGTTAAAAGCTTTAATCGCAATGAATG

CTAATAACTAACTAACCAAGATCTGTACCCCTTGGGGCCTCTAAAC

GGGTCTTGAGGGGTTTTTTGGATCCGAATTCACCGGTGCAATTCGT

AATCATGTCATAGCTGTTTCCTGTGTGAAATTGTTATCCGCTCACA

ATTCCACACAACATACGAGCCGGAAGCATAAAGTGTAAAGCCTGG

GGTGCCTAATGAGTGAGCTAACTCACATTAATTGCGTTGCGCTCAC

```
TGCCCGCTTTCCAGTCGGGAAACCTGTCGTGCCAGCTGCATTAATG
AATCGGCCAACGCGCGGGGAGAGGCGGTTTGCGTATTGGGCGCTC
TTCCGCTTCCTCGCTCACTGACTCGCTGCGCTCGGTCGTTCGGCTGC
GGCGAGCGGTATCAGCTCACTCAAAGGCGGTAATACGGTTATCCAC
AGAATCAGGGGATAACGCAGGAAAGAACATGTGAGCAAAAGGCC
AGCAAAAGGCCAGGAACCGTAAAAAGGCCGCGTTGCTGGCGTTTT
TCCATAGGCTCCGCCCCCCTGACGAGCATCACAAAAATCGACGCTC
AAGTCAGAGGTGGCGAAACCCGACAGGACTATAAAGATACCAGGC
GTTTCCCCCTGGAAGCTCCCTCGTGCGCTCTCCTGTTCCGACCCTGC
CGCTTACCGGATACCTGTCCGCCTTTCTCCCTTCGGGAAGCGTGGC
GCTTTCTCATAGCTCACGCTGTAGGTATCTCAGTTCGGTGTAGGTC
GTTCGCTCCAAGCTGGGCTGTGTGCACGAACCCCCCGTTCAGCCCG
ACCGCTGCGCCTTATCCGGTAACTATCGTCTTGAGTCCAACCCGGT
AAGACACGACTTATCGCCACTGGCAGCAGCCACTGGTAACAGGAT
TAGCAGAGCGAGGTATGTAGGCGGTGCTACAGAGTTCTTGAAGTG
GTGGCCTAACTACGGCTACACTAGAAGAACAGTATTTGGTATCTGC
GCTCTGCTGAAGCCAGTTACCTTCGGAAAAAGAGTTGGTAGCTCTT
GATCCGGCAAACAAACCACCGCTGGTAGCGGTGGTTTTTTTGTTTG
CAAGCAGCAGATTACGCGCAGAAAAAAAGGATCTCAAGAAGATCC
TTTGATCTTTTCTACGGGGTCTGACGCTCAGTGGAACGAAAACTCA
CGTTAAGGGATTTTGGTCATGAGATTATCAAAAAGGATCTTCACCT
AGATCCTTTTAAATTAAAAATGAAGTTTTAAATCAATCTAAAGTAT
ATATGAGTAAACTTGGTCTGACAGTTACCAATGCTTAATCAGTGAG
GCACCTATCTCAGCGATCTGTCTATTTCGTTCATCCATAGTTGCCTG
ACTCCCCGTCGTGTAGATAACTACGATACGGGAGGGCTTACCATCT
GGCCCCAGTGCTGCAATGATACCGCGAGACCCACGCTCACCGGCTC
CAGATTTATCAGCAATAAACCAGCCAGCCGGAAGGGCCGAGCGCA
GAAGTGGTCCTGCAACTTTATCCGCCTCCATCCAGTCTATTAATTGT
TGCCGGGAAGCTAGAGTAAGTAGTTCGCCAGTTAATAGTTTGCGCA
ACGTTGTTGCCATTGCTACAGGCATCGTGGTGTCACGCTCGTCGTT
TGGTATGGCTTCATTCAGCTCCGGTTCCCAACGATCAAGGCGAGTT
ACATGATCCCCCATGTTGTGCAAAAAAGCGGTTAGCTCCTTCGGTC
CTCCGATCGTTGTCAGAAGTAAGTTGGCCGCAGTGTTATCACTCAT
GGTTATGGCAGCACTGCATAATTCTCTTACTGTCATGCCATCCGTA
AGATGCTTTTCTGTGACTGGTGAGTACTCAACCAAGTCATTCTGAG
AATAGTGTATGCGGCGACCGAGTTGCTCTTGCCCGGCGTCAATACG
GGATAATACCGCGCCACATAGCAGAACTTTAAAAGTGCTCATCATT
GGAAAACGTTCTTCGGGGCGAAAACTCTCAAGGATCTTACCGCTGT
TGAGATCCAGTTCGATGTAACCCACTCGTGCACCCAACTGATCTTC
AGCATCTTTTACTTTCACCAGCGTTTCTGGGTGAGCAAAAACAGGA
AGGCAAATGCCGCAAAAAAGGGAATAAGGGCGACACGGAAATG
TTGAATACTCATACTCTTCCTTTTTCAATATTATTGAAGCATTTATC
AGGGTTATTGTCTCATGAGCGGATACATATTTGAATGTATTTAGAA
AAATAAACAAATAGGGGTTCCGCGCACATTTCCCCGAAAAGTGCC
ACCTGACGTCTAAGAAACCATTATTATCATGACATTAACCTATAAA
AATAGGCGTATCACGAGGCCCTTTCGTC
```

Figure 8:
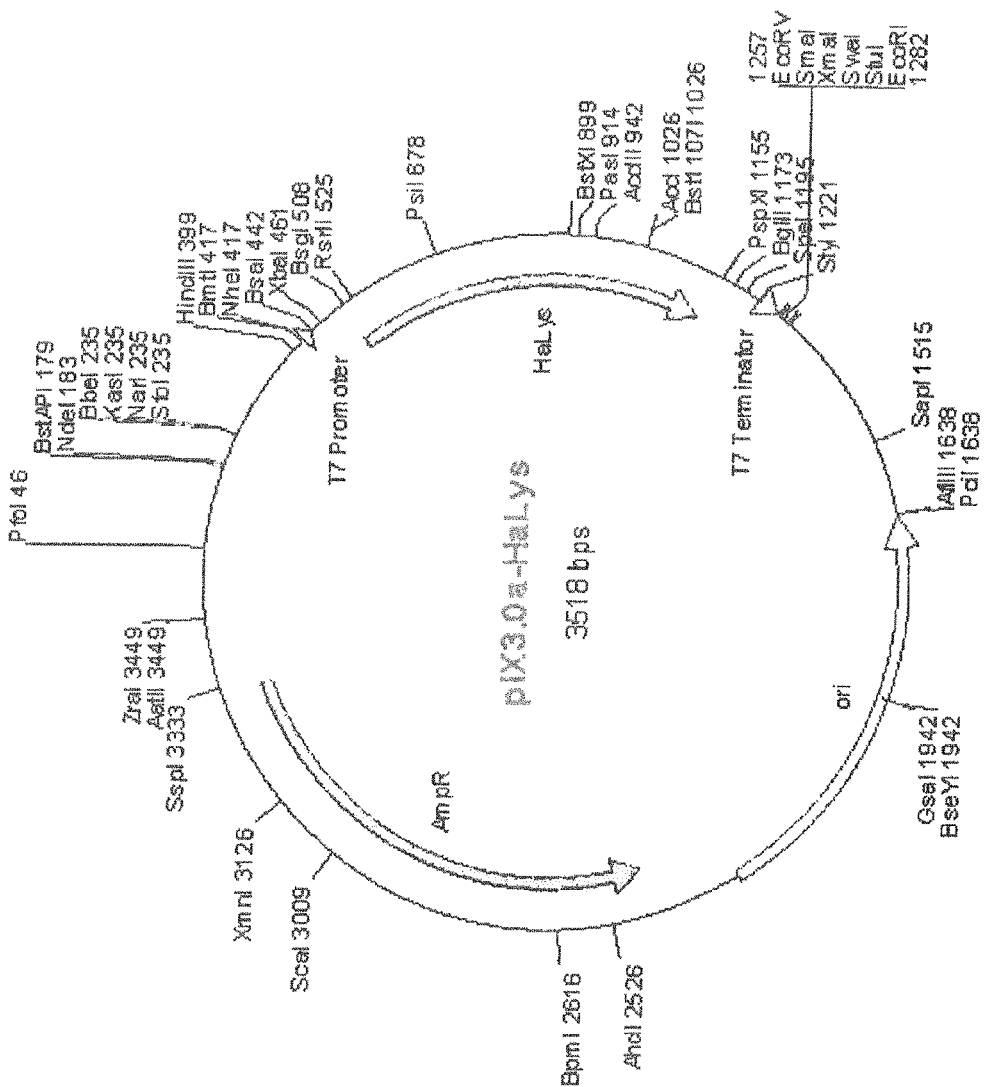
FIG. 8 shows the plasmid pIX3.0a-HaLys (plasmid DNA) having SEQ.ID.NO: 4.

FIG. 8 shows the plasmid pIX3.0a-HaLys (plasmid DNA) with the following sequence details:

| Type   | Start | End  | Name                                                  |
|--------|-------|------|-------------------------------------------------------|
| Region | 423   | 439  | T7 transcription promoter                             |
| Gene   | 502   | 1152 | HaLys, light chain anti-lysozyme Fab                  |
| Region | 1219  | 1257 | T7 transcription terminator                           |
| Region | 2313  | 1640 | complementary, replication origin (ori)               |
| Gene   | 3318  | 2458 | complementary, ampicillin resistance gene (β-lactamase) |

(SEQ. ID. NO: 4)
```
TCGCGCGTTTCGGTGATGACGGTGAAAACCTCTGACACATGCAGCT
CCCGGAGACGGTCACAGCTTGTCTGTAAGCGGATGCCGGGAGCAG
ACAAGCCCGTCAGGGCGCGTCAGCGGGTGTTGGCGGGTGTCGGG
CTGGCTTAACTATGCGGCATCAGAGCAGATTGTACTGAGAGTGCAC
CATATGCGGTGTGAAATACCGCACAGATGCGTAAGGAGAAAATAC
CGCATCAGGCGCCATTCGCCATTCAGGCTGCGCAACTGTTGGGAAG
GGCGATCGGTGCGGGCCTCTTCGCTATTACGCCAGCTGGCGAAAGG
GGGATGTGCTGCAAGGCGATTAAGTTGGGTAACGCCAGGGTTTTCC
CAGTCACGACGTTGTAAAACGACGGCCAGTGCCAAGCTTTCTCGAG
CGGCCGCTAGCTAATACGACTCACTATAGGGAGACCACAACGGTTT
CCCTCTAGAAATAATTTTGTTTAACTTTAAGAAGGAGATAAACAAT
GGATGTGCAGCTGCAGGAAAGCGGTCCGAGCCTGGTTAAACCGAG
CCAGACCCTGAGCCTGACCTGTAGCGTTACCGGTGATAGCATTACC
AGCGATTATTGGAGCTGGATTCGTAAATTTCCGGGTAATCGTCTGG
AATATATGGGTTATGTTAGCTATAGCGGCAGCACCTATTATAATCC
GAGCCTGAAAAGCCGTATTAGCATTACCCGTGATACCAGCAAAAA
TCAGTATTATCTGGATCTGAATAGCGTGACCACCGAAGATACCGCA
ACCTATTACTGTGCAAATTGGGATGGTGATTATTGGGGTCAGGGCA
CCCTGGTTACCGTTAGCGCAGCAAAAACCACACCGCCGAGCGTTTA
TCCGCTGGCACCGGGTAGCGCAGCACAGACCAATAGCATGGTTAC
CCTGGGTTGTCTGGTGAAAGGTTATTTTCCGGAACCGGTTACCGTT
```

-continued

```
ACCTGGAATAGCGGTAGCCTGAGCAGCGGTGTTCATACCTTTCCGG
CAGTTCTGCAGAGCGATCTGTATACCCTGAGCAGCAGCGTTACCGT
TCCGAGCAGTCCGCGTCCGAGCGAAACCGTTACCTGTAATGTTGCA
CATCCGGCAAGCAGCACCAAAGTTGATAAAAAAATTGTTCCGCGT
GATTGCTAATAACTCGAGCGGCCGCCTGCAGATCTAAATAATAAGT
AATTAACTAGTGAGCAATAACTAGCATAACCCCTTGGGGCCTCTAA
ACGGGTCTTGAGGGGTTTTTTGATATCCCGGGATTTAAATAGGCCT
GAATTCGTAATCATGGTCATAGCTGTTTCCTGTGTGAAATTGTTATC
CGCTCACAATTCCACACAACATACGAGCCGGAAGCATAAAGTGTA
AAGCCTGGGGTGCCTAATGAGTGAGCTAACTCACATTAATTGCGTT
GCGCTCACTGCCCGCTTTCCAGTCGGGAAACCTGTCGTGCCAGCTG
CATTAATGAATCGGCCAACGCGCGGGGAGAGGCGGTTTGCGTATT
GGGCGCTCTTCCGCTTCCTCGCTCACTGACTCGCTGCGCTCGGTCGT
TCGGCTGCGGCGAGCGGTATCAGCTCACTCAAAGGCGGTAATACG
GTTATCCACAGAATCAGGGGATAACGCAGGAAAGAACATGTGAGC
AAAAGGCCAGCAAAAGGCCAGGAACCGTAAAAAGGCCGCGTTGCT
GGCGTTTTTCCATAGGCTCCGCCCCCCTGACGAGCATCACAAAAAT
CGACGCTCAAGTCAGAGGTGGCGAAACCCGACAGGACTATAAAGA
TACCAGGCGTTTCCCCCTGGAAGCTCCCTCGTGCGCTCTCCTGTTCC
GACCCTGCCGCTTACCGGATACCTGTCCGCCTTTCTCCCTTCGGGA
AGCGTGGCGCTTTCTCATAGCTCACGCTGTAGGTATCTCAGTTCGG
TGTAGGTCGTTCGCTCCAAGCTGGGCTGTGTGCACGAACCCCCCGT
TCAGCCCGACCGCTGCGCCTTATCCGGTAACTATCGTCTTGAGTCC
AACCCGGTAAGACACGACTTATCGCCACTGGCAGCAGCCACTGGT
AACAGGATTAGCAGAGCGAGGTATGTAGGCGGTGCTACAGAGTTC
TTGAAGTGGTGGCCTAACTACGGCTACACTAGAAGGACAGTATTTG
GTATCTGCGCTCTGCTGAAGCCAGTTACCTTCGGAAAAAGAGTTGG
TAGCTCTTGATCCGGCAAACAAACCACCGCTGGTAGCGGTGGTTTT
TTTGTTTGCAAGCAGCAGATTACGCGCAGAAAAAAAGGATCTCAA
GAAGATCCTTTGATCTTTTCTACGGGGTCTGACGCTCAGTGGAACG
AAAACTCACGTTAAGGGATTTTGGTCATGAGATTATCAAAAAGGAT
CTTCACCTAGATCCTTTTAAATTAAAAATGAAGTTTTAAATCAATC
TAAAGTATATATGAGTAAACTTGGTCTGACAGTTACCAATGCTTAA
TCAGTGAGGCACCTATCTCAGCGATCTGTCTATTTCGTTCATCCATA
GTTGCCTGACTCCCCGTCGTGTAGATAACTACGATACGGGAGGGCT
TACCATCTGGCCCCAGTGCTGCAATGATACCGCGAGATCCACGCTC
ACCGGCTCCAGATTTATCAGCAATAAACCAGCCAGCCGGAAGGGC
CGAGCGCAGAAGTGGTCCTGCAACTTTATCCGCCTCCATCCAGTCT
ATTAATTGTTGCCGGGAAGCTAGAGTAAGTAGTTCGCCAGTTAATA
GTTTGCGCAACGTTGTTGCCATTGCTACAGGCATCGTGGTGTCACG
CTCGTCGTTTGGTATGGCTTCATTCAGCTCCGGTTCCCAACGATCA
AGGCGAGTTACATGATCCCCCATGTTGTGCAAAAAAGCGGTTAGCT
CCTTCGGTCCTCCGATCGTTGTCAGAAGTAAGTTGGCCGCAGTGTT
ATCACTCATGGTTATGGCAGCACTGCATAATTCTCTTACTGTCATG
CCATCCGTAAGATGCTTTTCTGTGACTGGTGAGTACTCAACCAAGT
CATTCTGAGAATAGTGTATGCGGCGACCGAGTTGCTCTTGCCCGGC
GTCAATACGGGATAATACCGCGCCACATAGCAGAACTTTAAAAGT
GCTCATCATTGGAAAACGTTCTTCGGGGCGAAAACTCTCAAGGATC
TTACCGCTGTTGAGATCCAGTTCGATGTAACCCACTCGTGCACCCA
ACTGATCTTCAGCATCTTTTACTTTCACCAGCGTTTCTGGGTGAGCA
AAAACAGGAAGGCAAAATGCCGCAAAAAAGGGAATAAGGGCGAC
ACGGAAATGTTGAATACTCATACTCTTCCTTTTTCAATATTATTGAA
GCATTTATCAGGGTTATTGTCTCATGAGCGGATACATATTTGAATG
TATTTAGAAAAATAAACAAATAGGGGTTCCGCGCACATTTCCCCGA
AAAGTGCCACCTGACGTCTAAGAAACCATTATTATCATGACATTAA
CCTATAAAAATAGGCGTATCACGAGGCCCTTTCGTC
```

Figure 9:
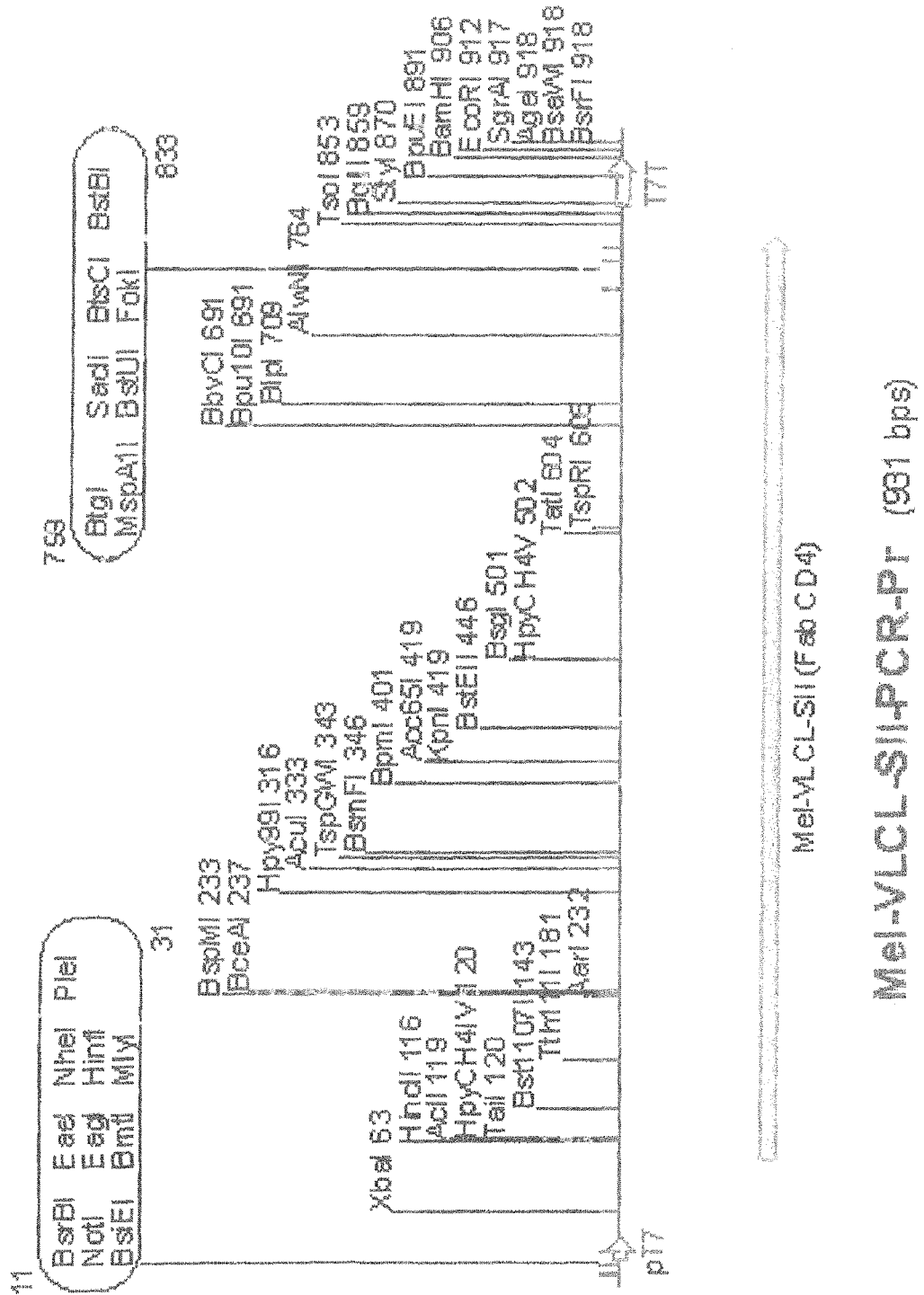
FIG. 9 shows the employed matrix Mel-VLCL-SII, linear, PCR-generated DNA having SEQ.ID.NO: 5.

FIG. 9 shows the employed matrix Mel-VLCL-SII, linear, PCR-generated DNA with the following sequence details:

| Type | Start | End | Name |
|---|---|---|---|
| Region | 25 | 41 | T7 transcription promoter |
| Gen | 104 | 844 | Mel-LaLys, light chain anti-lysozyme Fab with melittin signal peptide, C-terminal strep-tag |
| Region | 868 | 906 | T7 transcription terminator |

(SEQ. ID. NO: 5)
```
ATGATATCTCGAGCGGCCGCTAGCTAATACGACTCACTATAGGGAG
ACCACAACGGTTTCCCTCTAGAAATAATTTTGTTTAACTTTAAGAA
GGAGATAAACAATGAAATTCTTAGTCAACGTTGCCCTTGTTTTTAT
GGTCGTATACATTTCTTACATCTATGCGGACGATATCCAGATGACC
CAGTCTCCGGCTTCTCTGTCTGCTTCTGTTGGTGAAACCGTTACCTT
CACCTGCCGTGCTTCTGAAATGATCTACTCTTACCTGGCTTGGTATC
AGCAGAAACAGGGTAAATCTCCGCAACTGCTGGTTCACGACGCTA
AAACCCTGGCTGAAGGTGTTCCGTCCCGTTTCTCTGGTGGTGGTTC
TGGCACCCAGTTCTCTCTGAAAATCAACACCCTCCAGCCGGAAGAC
TTCGGTACCTACTACTGCCAGCACCACTACGGTAACCCGCCGACCT
TCGGTGGTGGCACCAAACTCGAGATCAAACGGGGATCGCTGCAC
CATCTGTCTTCATCTTCCCGCCATCTGATGAGCAGTTGAAATCTGG
AACTGCCTCTGTTGTGCCTGCTGAATAACTTCTATCCCAGAGAG
GCCAAAGTACAGTGGAAGGTGGATAACGCCCTCCAATCGGGTAAC
```

TCCCAGGAGAGTGTCACAGAGCAGGACAGCAAGGACAGCACCTAC

AGCCTCAGCAGCACCCTGACGCTGAGCAAAGCAGACTACGAGAAA

CACAAAGTCTACGCCTGCGAAGTCACCCATCAGGGCCTGAGTTCGC

CCGTCACAAAGAGCTTCAACCGCGGAGAGTGTTCTGCCTGGTCTCA

TCCGCAATTCGAAAAATAATAACTAACTAACCAAGATCTGTACCCC

TTGGGGCCTCTAAACGGGTCTTGAGGGGTTTTTTGGATCCGAATTC

ACCGGTGATATCAT

Figure 10:
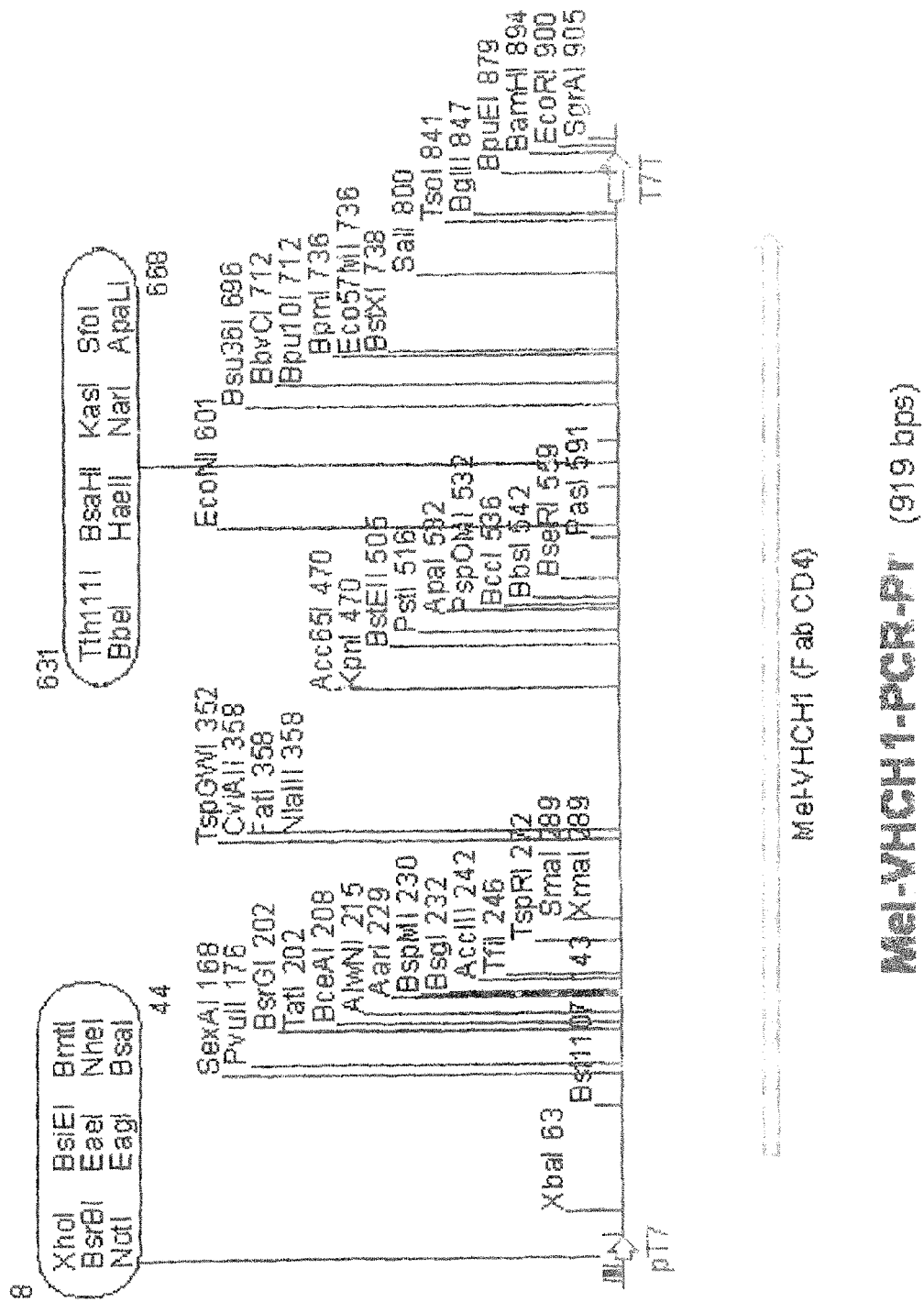
FIG. 10 shows the matrix Mel-VHCH1, linear, PCR-generated DNA having SEQ.ID.NO: 6.

FIG. 10 shows the matrix Mel-VHCH1, linear, PCR-generated DNA, with the following sequence details:

| Type   | Start | End | Name                                                            |
|--------|-------|-----|-----------------------------------------------------------------|
| Region | 25    | 41  | T7 transcription promoter                                       |
| Gene   | 104   | 832 | Mel-HaLys, heavy chain anti-lysozyme Fab with melittin signal peptide |
| Region | 856   | 894 | T7 transcription terminator                                     |

(SEQ. ID. NO: 6)
ATGATATCTCGAGCGGCCGCTAGCTAATACGACTCACTATAGGGAG

ACCACAACGGTTTCCCTCTAGAAATAATTTTGTTTAACTTTAAGAA

GGAGATAAACAATGAAATTCTTAGTCAACGTTGCCCTTGTTTTTAT

GGTCGTATACATTTCTTACATCTATGCGGACCAGGTTCAGCTGAAA

CAGTCTGGTCCGGGTCTTGTACAGCCGTCCCAGTCTCTGTCTATCA

CCTGCACCGTTTCCGGATTCTCTCTGACCACCTTCGGTGTTCACTGG

GTTCGTCAGTCCCCGGGTAAAGGTCTGGAATGGCTGGGTGTTATCT

GGCGTTCTGGTATCACCGACTACAACGTTCCGTTCATGTCTCGTCT

GTCTATCACCAAAGACAACTCTAAATCTCAGGTTTTCTTCAAACTG

AACTCTCTGCAACCGGACGACACCGCTATCTACTACTGCGCTAAAA

ACGATCCGGGTACCGGTTTCGCTTACTGGGGTCAGGGCACCCTGGT

CACCGTTTCTGCAGGGAGCACCAAGGGCCCATCGGTCTTCCCCCTG

GCACCCTCCTCCAAGAGCACCTCTGGGGGCACAGCGGCCCTGGGCT

GCCTGGTCAAGGACTACTTCCCCGAACCGGTGACGGTGTCGTGGAA

CTCAGGCGCCCTGACCAGCGGCGTGCACACCTTCCCGGCTGTCCTA

CAGTCCTCAGGACTCTACTCCCTCAGCAGCGTGGTGACTGTGCCCT

CCAGCAGCTTGGGCACCCAGACCTACATCTGCAACGTTAATCACAA

ACCCAGCAACACCAAGGTCGACAAGAAAGTTGAGCCCAAATCTTG

CTAATAACTAACTAACCAAGATCTGTACCCCTTGGGGCCTCTAAAC

GGGTCTTGAGGGGTTTTTTGGATCCGAATTCACCGGTGATATCAT

The invention claimed is:

1. A method for producing a dimeric monoclonal antibody or physiologically effective antibody fragment containing internal or external disulfide bonds, comprising the following steps:
   a) providing a cell-free lysate, obtained from eukaryotic cells selected from the group consisting of insect cells, HeLa cells, CHO cells, HEK cells, wheat germ cells, rabbit reticulocyte cells, yeast cells, protozoa cells and green alga, which contains functional microsomal vesicles,
   b) adding a nucleic acid coding the dimeric monoclonal antibody or antibody fragment to the lysate wherein said nucleic acid comprises a signal sequence capable of assisting the translocation of said antibody or antibody fragment formed with the nucleic acid into the microsomal vesicles,
   c) holding the lysate with the nucleic acid for a given time at a temperature in the range from 20° C. to 35° C., to allow the signal sequence to assist in the translocation of said antibody or said antibody fragment formed with the nucleic acid into the microsomal vesicles, and
   d) digesting the microsomal vesicles, whereby said antibodies or antibody fragments the proteins or peptides obtained thereby are optionally separated from the lysate.

2. The method according to claim 1, wherein the lysate does not contain any chaperones and/or protein disulfide isomerases, or wherein no chaperones and/or protein disulfide isomerases are added to the lysate.

3. The method according to claim 1, wherein the lysate is not subjected to any chemical pre-treatment for stabilizing the redox potential.

4. The method according to claim 1, wherein said cells are insect cells.

5. The method according to claim 1, wherein step c) is carried out below a temperature of 30° C., in particular below 26° C.

6. The method according to claim 1, wherein step c) is carried out for a time of 0.5 to 5 hours.

7. The method according to claim 1, wherein the nucleic acid is a linear DNA.

8. A preparation containing dimeric monoclonal antibodies or physiologically effective antibody fragments and a cell-free lysate, obtained from eukaryotic cells selected from the group consisting of insect cells, HeLa cells, CHO cells, HEK cells, wheat germ cells, rabbit reticulocyte cells, yeast cells, protozoa cells and green alga, wherein the lysate contains functional microsomal vesicles or a digest of such microsomal vesicles, and wherein the preparation does not contain any endogenous and/or added chaperones and/or protein disulfide isomerases.

* * * * *

SEQUENCE LISTING

```
<160> NUMBER OF SEQ ID NOS: 6

<210> SEQ ID NO 1
<211> LENGTH: 3774
<212> TYPE: DNA
<213> ORGANISM: Artificial
<220> FEATURE:
<223> OTHER INFORMATION: Plasmid

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttgcatgc aaggagatgg     420
cgcccaacag tcccccggcc acgggcctg ccaccatacc cacgccgaaa caagcgctca      480
tgagcccgaa gtggcgagcc cgatcttccc catcggtgat gtcggcgata taggcgccag     540
caaccgcacc tgtggcgccg gtgatgccgg ccacgatgcg tccggcgtag aggatcgaga     600
tcgatctcga tcccgcgaaa ttaatacgac tcactatagg gagaccacaa cggtttccct     660
ctagaaataa ttttgtttaa ctttaagaag gagatatacc atgaaattct tagtcaacgt     720
tgccctggtt tttatggtgg tgtatattag ctatatttat gccgatattg tgctgaccca     780
```

```
gagtccggca accctgagcg ttacaccggg taatagcgtt agcctgagct gtcgtgcaag    840
ccagagcatt ggtaataatc tgcattggta tcagcagaaa agccatgaaa gtccgcgtct    900
gctgattaaa tatgcaagcc agtcaattag cggtattccg agccgtttta gcggtagcgg    960
tagtggcacc gattttaccc tgagcattaa tagcgttgaa accgaagatt ttggcatgta   1020
tttttgccag cagagcaata gctggccgta tacctttggt ggtggcacca aactggaaat   1080
taaacgtgca gatgcagcac cgaccgttag cattttttcg ccgagcagcg aacagctgac   1140
cagcggtggt gcaagcgttg tttgttttct gaataacttt tatccgaaag atatcaatgt   1200
gaaatggaaa attgatggca gcgaacgtca gaatggtgtt ctgaatagct ggaccgatca   1260
ggatagcaaa gatagcacct atagcatgag cagcaccctg accctgacca agatgaata   1320
tgaacgccat aatagctata cctgtgaagc aacccataaa accagcacca gcccgattgt   1380
taaaagcttt aatcgcaatg aatgctaata actcgagcgg ccgcctgcag atctaaataa   1440
taagtaatta actagtgagc aataactagc ataaccccct tggggcctcta aacgggtctt   1500
gaggggtttt ttgatatccc gggatttaaa taggcctgaa ttcgtaatca tggtcatagc   1560
tgtttcctgt gtgaaattgt tatccgctca caattccaca caacatacga gccggaagca   1620
taaagtgtaa agcctgggt gcctaatgag tgagctaact cacattaatt gcgttgcgct   1680
cactgcccgc tttccagtcg ggaaacctgt cgtgccagct gcattaatga atcggccaac   1740
gcgcggggag aggcggtttg cgtattgggc gctcttccgc ttcctcgctc actgactcgc   1800
tgcgctcggt cgttcggctg cggcgagcgg tatcagctca ctcaaaggcg gtaatacggt   1860
tatccacaga atcaggggat aacgcaggaa agaacatgtg agcaaaaggc cagcaaaagg   1920
ccaggaaccg taaaaaggcc gcgttgctgg cgttttttcca taggctccgc ccccctgacg   1980
agcatcacaa aaatcgacgc tcaagtcaga ggtggcgaaa cccgacagga ctataaagat   2040
accaggcgtt ccccctgga agctccctcg tgcgctctcc tgttccgacc ctgccgctta   2100
ccggatacct gtccgccttt ctcccttcgg gaagcgtggc gctttctcat agctcacgct   2160
gtaggtatct cagttcggtg taggtcgttc gctccaagct gggctgtgtg cacgaacccc   2220
ccgttcagcc cgaccgctgc gccttatccg gtaactatcg tcttgagtcc aacccggtaa   2280
gacacgactt atcgccactg gcagcagcca ctggtaacag gattagcaga gcgaggtatg   2340
taggcggtgc tacagagttc ttgaagtggt ggcctaacta cggctacact agaaggacag   2400
tatttggtat ctgcgctctg ctgaagccag ttaccttcgg aaaaagagtt ggtagctctt   2460
gatccggcaa acaaaccacc gctggtagcg gtggtttttt tgtttgcaag cagcagatta   2520
cgcgcagaaa aaaggatctc aagaagatc ctttgatctt ttctacgggg tctgacgctc   2580
agtggaacga aaactcacgt taagggattt tggtcatgag attatcaaaa aggatcttca   2640
cctagatcct tttaaattaa aaatgaagtt ttaaatcaat ctaaagtata tatgagtaaa   2700
cttggtctga cagttaccaa tgcttaatca gtgaggcacc tatctcagcg atctgtctat   2760
ttcgttcatc catagttgcc tgactccccg tcgtgtagat aactacgata cgggagggct   2820
taccatctgg ccccagtgct gcaatgatac cgcgagatcc acgctcaccg gctccagatt   2880
tatcagcaat aaaccagcca gccggaaggg ccgagcgcag aagtggtcct gcaactttat   2940
ccgcctccat ccagtctatt aattgttgcc gggaagctag agtaagtagt tcgccagtta   3000
atagtttgcg caacgttgtt gccattgcta caggcatcgt ggtgtcacgc tcgtcgtttg   3060
gtatggcttc attcagctcc ggttcccaac gatcaaggcg agttacatga tcccccatgt   3120
tgtgcaaaaa agcggttagc tccttcggtc ctccgatcgt tgtcagaagt aagttggccg   3180
```

```
cagtgttatc actcatggtt atggcagcac tgcataattc tcttactgtc atgccatccg    3240
taagatgctt ttctgtgact ggtgagtact caaccaagtc attctgagaa tagtgtatgc    3300
ggcgaccgag ttgctcttgc ccggcgtcaa tacgggataa taccgcgcca catagcagaa    3360
ctttaaaagt gctcatcatt ggaaaacgtt cttcggggcg aaaactctca aggatcttac    3420
cgctgttgag atccagttcg atgtaaccca ctcgtgcacc caactgatct tcagcatctt    3480
ttactttcac cagcgtttct gggtgagcaa aaacaggaag gcaaaatgcc gcaaaaaagg    3540
gaataagggc gacacggaaa tgttgaatac tcatactctt cctttttcaa tattattgaa    3600
gcatttatca gggttattgt ctcatgagcg gatacatatt tgaatgtatt tagaaaaata    3660
aacaaatagg ggttccgcgc acatttcccc gaaaagtgcc acctgacgtc taagaaacca    3720
ttattatcat gacattaacc tataaaaata ggcgtatcac gaggccctt cgtc         3774

<210> SEQ ID NO 2
<211> LENGTH: 3777
<212> TYPE: DNA
<213> ORGANISM: Artificial
<220> FEATURE:
<223> OTHER INFORMATION: Plasmid

<400> SEQUENCE: 2
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttgcatgc aaggagatgg     420
cgcccaacag tcccccggcc acggggcctg ccaccatacc cacgccgaaa caagcgctca     480
tgagcccgaa gtggcgagcc cgatcttccc catcggtgat gtcggcgata taggcgccag     540
caaccgcacc tgtggcgccg gtgatgccgg ccacgatgcg tccggcgtag aggatcgaga     600
tcgatctcga tcccgcgaaa ttaatacgac tcactatagg gagaccacaa cggtttccct     660
ctagaaataa ttttgtttaa ctttaagaag gagatatacc atgaaattct tagtcaacgt     720 tgcccctggtt tttatggtgg tgtatattag ctatatttat gccgatgtgc agctgcagga     780
aagcggtccg agcctggtta aaccgagcca gaccctgagc ctgacctgta gcgttaccgg     840
tgatagcatt accagcgatt attggagctg gattcgtaaa tttccgggta atcgtctgga     900
atatatgggt tatgttagct atagcggcag cacctattat aatccgagcc tgaaaagccg     960
tattagcatt acccgtgata ccagcaaaaa tcagtattat ctggatctga atagcgtgac    1020
caccgaagat accgcaacct attactgtgc aaattgggat ggtgattatt ggggtcaggg    1080
caccctggtt accgttagcg cagcaaaaac cacaccgccg agcgtttatc cgctggcacc    1140
gggtagcgca gcacagacca atagcatggt taccctgggt tgtctggtga aaggttattt    1200
tccggaaccg gttaccgtta cctggaatag cggtagcctg agcagcggtg ttcatacctt    1260
tccggcagtt ctgcagagcg atctgtatac cctgagcagc agcgttaccg ttccgagcag    1320
tccgcgtccg agcgaaaccg ttacctgtaa tgttgcacat ccggcaagca gcaccaaagt    1380
tgataaaaaa attgttccgc gtgattgcta ataactcgag cggccgcctg cagatctaaa    1440
```

```
taataagtaa ttaactagtg agcaataact agcataaccc cttggggcct ctaaacgggt  1500
cttgaggggt tttttgatat cccgggattt aaataggcct gaattcgtaa tcatggtcat  1560
agctgtttcc tgtgtgaaat tgttatccgc tcacaattcc acacaacata cgagccggaa  1620
gcataaagtg taaagcctgg ggtgcctaat gagtgagcta actcacatta attgcgttgc  1680
gctcactgcc cgctttccag tcgggaaacc tgtcgtgcca gctgcattaa tgaatcggcc  1740
aacgcgcggg gagaggcggt ttgcgtattg ggcgctcttc cgcttcctcg ctcactgact  1800
cgctgcgctc ggtcgttcgg ctgcggcgag cggtatcagc tcactcaaag gcggtaatac  1860
ggttatccac agaatcaggg gataacgcag gaaagaacat gtgagcaaaa ggccagcaaa  1920
aggccaggaa ccgtaaaaag gccgcgttgc tggcgttttt ccataggctc cgcccccctg  1980
acgagcatca aaaaatcga cgctcaagtc agaggtggcg aaacccgaca ggactataaa  2040
gataccaggc gtttccccct ggaagctccc tcgtgcgctc tcctgttccg accctgccgc  2100
ttaccggata cctgtccgcc tttctccctt cgggaagcgt ggcgctttct catagctcac  2160
gctgtaggta tctcagttcg gtgtaggtcg ttcgctccaa gctgggctgt gtgcacgaac  2220
cccccgttca gcccgaccgc tgcgccttat ccggtaacta tcgtcttgag tccaacccgg  2280
taagacacga cttatcgcca ctggcagcag ccactggtaa caggattagc agagcgaggt  2340
atgtaggcgg tgctacagag ttcttgaagt ggtggcctaa ctacggctac actagaagga  2400
cagtatttgg tatctgcgct ctgctgaagc cagttacctt cggaaaaaga gttggtagct  2460
cttgatccgg caaacaaacc accgctggta gcggtggttt ttttgtttgc aagcagcaga  2520
ttacgcgcag aaaaaaagga tctcaagaag atcctttgat cttttctacg ggtctgacg   2580
ctcagtggaa cgaaaactca cgttaaggga ttttggtcat gagattatca aaaaggatct  2640
tcacctagat ccttttaaat taaaaatgaa gttttaaatc aatctaaagt atatatgagt  2700
aaacttggtc tgacagttac caatgcttaa tcagtgaggc acctatctca gcgatctgtc  2760
tatttcgttc atccatagtt gcctgactcc ccgtcgtgta gataactacg atacgggagg  2820
gcttaccatc tggccccagt gctgcaatga taccgcgaga cccacgctca ccggctccag  2880
atttatcagc aataaaccag ccagccggaa gggccgagcg cagaagtggt cctgcaactt  2940
tatccgcctc catccagtct attaattgtt gccgggaagc tagagtaagt agttcgccag  3000
ttaatagttt gcgcaacgtt gttgccattg ctacaggcat cgtggtgtca cgctcgtcgt  3060
ttggtatggc ttcattcagc tccggttccc aacgatcaag gcgagttaca tgatccccca  3120
tgttgtgcaa aaaagcggtt agctccttcg gtcctccgat cgttgtcaga agtaagttgg  3180
ccgcagtgtt atcactcatg gttatggcag cactgcataa ttctcttact gtcatgccat  3240
ccgtaagatg cttttctgtg actggtgagt actcaaccaa gtcattctga atagtgta    3300
tgcggcgacc gagttgctct tgcccggcgt caatacggga taataccgcg ccacatagca  3360
gaactttaaa agtgctcatc attggaaaac gttcttcggg gcgaaaactc tcaaggatct  3420
taccgctgtt gagatccagt tcgatgtaac ccactcgtgc acccaactga tcttcagcat  3480
cttttacttt caccagcgtt tctgggtgag caaaaacagg aaggcaaaat gccgcaaaaa  3540
agggaataag ggcgacacgg aaatgttgaa tactcatact cttccttttt caatattatt  3600
gaagcattta tcagggttat tgtctcatga gcggatacat atttgaatgt atttagaaaa  3660
ataaacaaat aggggttccg cgcacatttc cccgaaaagt gccacctgac gtctaagaaa  3720
ccattattat catgacatta acctataaaa ataggcgtat cacgaggccc tttcgtc     3777
```

<210> SEQ ID NO 3
<211> LENGTH: 3465
<212> TYPE: DNA
<213> ORGANISM: Artificial
<220> FEATURE:
<223> OTHER INFORMATION: Plasmid

<400> SEQUENCE: 3

| | | | | | | |
|---|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccaa | gctttctcga | gcggccgcta | 420 |
| gctaatacga | ctcactatag | ggagaccaca | acggtttccc | tctagaaata | attttgttta | 480 |
| actttaagaa | ggagatataaac | aatggatatt | gtgctgaccc | agagtccggc | aaccctgagc | 540 |
| gttacaccgg | gtaatagcgt | tagcctgagc | tgtcgtgcaa | gccagagcat | tggtaataat | 600 |
| ctgcattggt | atcagcagaa | aagccatgaa | agtccgcgtc | tgctgattaa | atatgcaagc | 660 |
| cagtcaatta | gcggtattcc | gagccgtttt | agcggtagcg | gtagtggcac | cgattttacc | 720 |
| ctgagcatta | tagcgttga | accgaagat | tttggcatgt | attttgcca | gcagagcaat | 780 |
| agctggccgt | atacctttgg | tggtggcacc | aaactggaaa | ttaaacgtgc | agatgcagca | 840 |
| ccgaccgtta | gcattttcc | gccgagcagc | gaacagctga | ccagcggtgg | tgcaagcgtt | 900 |
| gtttgttttc | tgaataactt | ttatccgaaa | gatatcaatg | tgaaatggaa | aattgatggc | 960 |
| agcgaacgtc | agaatggtgt | tctgaatagc | tggaccgatc | aggatagcaa | agatagcacc | 1020 |
| tatagcatga | gcagcacccct | gaccctgacc | aaagatgaat | atgaacgcca | taatagctat | 1080 |
| acctgtgaag | caacccataa | aaccagcacc | agcccgattg | ttaaaagctt | taatcgcaat | 1140 |
| gaatgctaat | aactaactaa | ccaagatctg | taccccttgg | ggcctctaaa | cgggtcttga | 1200 |
| ggggttttt | ggatccgaat | tcaccggtgc | aattcgtaat | catgtcatag | ctgtttcctg | 1260 |
| tgtgaaattg | ttatccgctc | acaattccac | acaacatacg | agccggaagc | ataaagtgta | 1320 |
| aagcctgggg | tgcctaatga | gtgagctaac | tcacattaat | tgcgttgcgc | tcactgcccg | 1380 |
| ctttccagtc | gggaaacctg | tcgtgccagc | tgcattaatg | aatcggccaa | cgcgcgggga | 1440 |
| gaggcggttt | gcgtattggg | cgctcttccg | cttcctcgct | cactgactcg | ctgcgctcgg | 1500 |
| tcgttcggct | gcggcgagcg | gtatcagctc | actcaaaggc | ggtaatacgg | ttatccacag | 1560 |
| aatcagggga | taacgcagga | aagaacatgt | gagcaaaagg | ccagcaaaag | gccaggaacc | 1620 |
| gtaaaaaggc | cgcgttgctg | gcgtttttcc | ataggctccg | ccccctgac | gagcatcaca | 1680 |
| aaaatcgacg | ctcaagtcag | aggtggcgaa | acccgacagg | actataaaga | taccaggcgt | 1740 |
| ttccccctgg | aagctccctc | gtgcgctctc | ctgttccgac | cctgccgctt | accggatacc | 1800 |
| tgtccgcctt | tctcccttcg | ggaagcgtgg | cgctttctca | tagctcacgc | tgtaggtatc | 1860 |
| tcagttcggt | gtaggtcgtt | cgctccaagc | tgggctgtgt | gcacgaaccc | cccgttcagc | 1920 |
| ccgaccgctg | cgccttatcc | ggtaactatc | gtcttgagtc | caacccggta | agacacgact | 1980 |
| tatcgccact | ggcagcagcc | actggtaaca | ggattagcag | agcgaggtat | gtaggcggtg | 2040 |
| ctacagagtt | cttgaagtgg | tggcctaact | acggctacac | tagaagaaca | gtatttggta | 2100 |

```
tctgcgctct gctgaagcca gttaccttcg aaaaagagt  tggtagctct tgatccggca    2160
aacaaaccac cgctggtagc ggtggttttt ttgtttgcaa gcagcagatt acgcgcagaa    2220
aaaaaggatc tcaagaagat cctttgatct tttctacggg gtctgacgct cagtggaacg    2280
aaaactcacg ttaagggatt ttggtcatga gattatcaaa aaggatcttc acctagatcc    2340
ttttaaatta aaaatgaagt tttaaatcaa tctaaagtat atatgagtaa acttggtctg    2400
acagttacca atgcttaatc agtgaggcac ctatctcagc gatctgtcta tttcgttcat    2460
ccatagttgc ctgactcccc gtcgtgtaga taactacgat acgggagggc ttaccatctg    2520
gccccagtgc tgcaatgata ccgcgagacc cacgctcacc ggctccagat ttatcagcaa    2580
taaaccagcc agccggaagg gccgagcgca gaagtggtcc tgcaacttta tccgcctcca    2640
tccagtctat taattgttgc cgggaagcta gagtaagtag ttcgccagtt aatagtttgc    2700
gcaacgttgt tgccattgct acaggcatcg tggtgtcacg ctcgtcgttt ggtatggctt    2760
cattcagctc cggttcccaa cgatcaaggc gagttacatg atcccccatg ttgtgcaaaa    2820
aagcggttag ctccttcggt cctccgatcg ttgtcagaag taagttggcc gcagtgttat    2880
cactcatggt tatggcagca ctgcataatt ctcttactgt catgccatcc gtaagatgct    2940
tttctgtgac tggtgagtac tcaaccaagt cattctgaga atagtgtatg cggcgaccga    3000
gttgctcttg cccggcgtca atacgggata taccgcgcc  acatagcaga actttaaaag    3060
tgctcatcat tggaaaacgt tcttcggggc gaaaactctc aaggatctta ccgctgttga    3120
gatccagttc gatgtaaccc actcgtgcac ccaactgatc ttcagcatct tttactttca    3180
ccagcgtttc tgggtgagca aaaacaggaa ggcaaaatgc cgcaaaaaag gaataaggg     3240 cgacacggaa atgttgaata ctcatactct tcctttttca atattattga agcatttatc    3300
agggttattg tctcatgagc ggatacatat ttgaatgtat ttagaaaaat aaacaaatag    3360
gggttccgcg cacatttccc cgaaaagtgc cacctgacgt ctaagaaacc attattatca    3420
tgacattaac ctataaaaat aggcgtatca cgaggccctt tcgtc                    3465

<210> SEQ ID NO 4
<211> LENGTH: 3518
<212> TYPE: DNA
<213> ORGANISM: Artificial
<220> FEATURE:
<223> OTHER INFORMATION: Plasmid

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gctttctcga gcggccgcta     420
gctaatacga ctcactatag ggagaccaca acggtttccc tctagaaata attttgttta     480
actttaagaa ggagatataa catggatgtg cagctgcagg aaagcggtcc gagcctggtt     540
aaaccgagcc agaccctgag cctgacctgt agcgttaccg gtgatagcat taccagcgat     600
tattggagct ggattcgtaa atttccgggt aatcgtctgg aatatatggg ttatgttagc     660
tatagcggca gcaccctatta taatccgagc ctgaaaagcc gtattagcat tacccgtgat     720
```

```
accagcaaaa atcagtatta tctggatctg aatagcgtga ccaccgaaga taccgcaacc    780
tattactgtg caaattggga tggtgattat tggggtcagg gcaccctggt taccgttagc    840
gcagcaaaaa ccacaccgcc gagcgtttat ccgctggcac cgggtagcgc agcacagacc    900
aatagcatgg ttaccctggg ttgtctggtg aaaggttatt ttccggaacc ggttaccgtt    960
acctggaata gcggtagcct gagcagcggt gttcatacct ttccggcagt tctgcagagc   1020
gatctgtata ccctgagcag cagcgttacc gttccgagca gtccgcgtcc gagcgaaacc   1080
gttacctgta atgttgcaca tccggcaagc agcaccaaag ttgataaaaa aattgttccg   1140
cgtgattgct aataactcga gcggccgcct gcagatctaa ataataagta attaactagt   1200
gagcaataac tagcataacc ccttggggcc tctaaacggg tcttgagggg ttttttgata   1260
tcccgggatt taaataggcc tgaattcgta atcatggtca tagctgtttc ctgtgtgaaa   1320
ttgttatccg ctcacaattc cacacaacat acgagccgga agcataaagt gtaaagcctg   1380
gggtgcctaa tgagtgagct aactcacatt aattgcgttg cgctcactgc ccgctttcca   1440
gtcgggaaac ctgtcgtgcc agctgcatta atgaatcggc caacgcgcgg ggagaggcgg   1500
tttgcgtatt gggcgctctt ccgcttcctc gctcactgac tcgctgcgct cggtcgttcg   1560
gctgcggcga gcggtatcag ctcactcaaa ggcggtaata cggttatcca cagaatcagg   1620
ggataacgca ggaaagaaca tgtgagcaaa aggccagcaa aaggccagga accgtaaaaa   1680
ggccgcgttg ctggcgtttt tccataggct ccgcccccct gacgagcatc acaaaaatcg   1740
acgctcaagt cagaggtggc gaaacccgac aggactataa agataccagg cgtttccccc   1800
tggaagctcc ctcgtgcgct ctcctgttcc gaccctgccg cttaccggat acctgtccgc   1860
ctttctccct tcgggaagcg tggcgctttc tcatagctca cgctgtaggt atctcagttc   1920
ggtgtaggtc gttcgctcca agctgggctg tgtgcacgaa ccccccgttc agcccgaccg   1980
ctgcgcctta tccggtaact atcgtcttga gtccaacccg gtaagacacg acttatcgcc   2040
actggcagca gccactggta acaggattag cagagcgagg tatgtaggcg gtgctacaga   2100
gttcttgaag tggtggccta actacggcta cactagaagg acagtatttg gtatctgcgc   2160
tctgctgaag ccagttacct tcggaaaaag agttggtagc tcttgatccg gcaaacaaac   2220
caccgctggt agcggtggtt tttttgtttg caagcagcag attacgcgca gaaaaaaagg   2280
atctcaagaa gatcctttga tcttttctac ggggtctgac gctcagtgga acgaaaactc   2340
acgttaaggg attttggtca tgagattatc aaaaaggatc ttcacctaga tccttttaaa   2400
ttaaaaatga agttttaaat caatctaaag tatatatgag taaacttggt ctgacagtta   2460
ccaatgctta atcagtgagg cacctatctc agcgatctgt ctatttcgtt catccatagt   2520
tgcctgactc cccgtcgtgt agataactac gatacgggag ggcttaccat ctggccccag   2580
tgctgcaatg ataccgcgag atccacgctc accggctcca gatttatcag caataaacca   2640
gccagccgga agggccgagc gcagaagtgg tcctgcaact ttatccgcct ccatccagtc   2700
tattaattgt tgccgggaag ctagagtaag tagttcgcca gttaatagtt tgcgcaacgt   2760
tgttgccatt gctacaggca tcgtggtgtc acgctcgtcg tttggtatgg cttcattcag   2820
ctccggttcc caacgatcaa ggcgagttac atgatccccc atgttgtgca aaaaagcggt   2880
tagctccttc ggtcctccga tcgttgtcag aagtaagttg gccgcagtgt tatcactcat   2940
ggttatggca gcactgcata attctcttac tgtcatgcca tccgtaagat gcttttctgt   3000
gactggtgag tactcaacca agtcattctg agaatagtgt atgcggcgac cgagttgctc   3060
```

```
ttgcccggcg tcaatacggg ataataccgc gccacatagc agaactttaa aagtgctcat    3120
cattggaaaa cgttcttcgg ggcgaaaact ctcaaggatc ttaccgctgt tgagatccag    3180
ttcgatgtaa cccactcgtg cacccaactg atcttcagca tctttttactt tcaccagcgt    3240 ttctgggtga gcaaaaacag gaaggcaaaa tgccgcaaaa aagggaataa gggcgacacg    3300
gaaatgttga atactcatac tcttcctttt tcaatattat tgaagcattt atcagggtta    3360
ttgtctcatg agcggataca tatttgaatg tatttagaaa aataaacaaa tagggggttcc    3420 gcgcacattt ccccgaaaag tgccacctga cgtctaagaa accattatta tcatgacatt    3480
aacctataaa aataggcgta tcacgaggcc ctttcgtc                           3518
```

<210> SEQ ID NO 5
<211> LENGTH: 931
<212> TYPE: DNA
<213> ORGANISM: Artificial
<220> FEATURE:
<223> OTHER INFORMATION: Plasmid

<400> SEQUENCE: 5

```
atgatatctc gagcggccgc tagctaatac gactcactat agggagacca caacggtttc     60
cctctagaaa taattttgtt taactttaag aaggagataa acaatgaaat tcttagtcaa    120
cgttgccctt gtttttatgg tcgtatacat ttcttacatc tatgcggacg atatccagat    180
gacccagtct ccggcttctc tgtctgcttc tgttggtgaa accgttacct tcacctgccg    240
tgcttctgaa atgatctact cttacctggc ttggtatcag cagaaacagg gtaaatctcc    300
gcaactgctg gttcacgacg ctaaaaccct ggctgaaggt gttccgtccc gtttctctgg    360
tggtggttct ggcacccagt tctctctgaa aatcaacacc ctccagccgg aagacttcgg    420
tacctactac tgccagcacc actacggtaa cccgccgacc ttcggtggtg gcaccaaact    480
cgagatcaaa cggggggatcg ctgcaccatc tgtcttcatc ttcccgccat ctgatgagca    540
gttgaaatct ggaactgcct ctgttgtgtg cctgctgaat aacttctatc ccagagaggc    600
caaagtacag tggaaggtgg ataacgccct ccaatcgggt aactcccagg agagtgtcac    660
agagcaggac agcaaggaca gcacctcag cctcagcagc accctgacgc tgagcaaagc    720
agactacgag aaacacaaag tctacgcctg cgaagtcacc catcagggcc tgagttcgcc    780
cgtcacaaag agcttcaacc gcggagagtg ttctgcctgg tctcatccgc aattcgaaaa    840
ataataacta actaaccaag atctgtaccc cttggggcct ctaaacgggt cttgaggggt    900
tttttggatc cgaattcacc ggtgatatca t                                   931
```

<210> SEQ ID NO 6
<211> LENGTH: 919
<212> TYPE: DNA
<213> ORGANISM: Artificial
<220> FEATURE:
<223> OTHER INFORMATION: Plasmid

<400> SEQUENCE: 6

```
atgatatctc gagcggccgc tagctaatac gactcactat agggagacca caacggtttc     60
cctctagaaa taattttgtt taactttaag aaggagataa acaatgaaat tcttagtcaa    120
cgttgccctt gtttttatgg tcgtatacat ttcttacatc tatgcggacc aggttcagct    180
gaaacagtct ggtccgggtc ttgtacagcc gtcccagtct ctgtctatca cctgcaccgt    240
ttccggattc tctctgacca ccttcggtgt tcactgggtt cgtcagtccc cgggtaaagg    300
tctggaatgg ctgggtgtta tctggcgttc tggtatcacc gactacaacg ttccgttcat    360
```

```
gtctcgtctg tctatcacca aagacaactc taaatctcag gttttcttca aactgaactc      420
tctgcaaccg gacgacaccg ctatctacta ctgcgctaaa aacgatccgg gtaccggttt      480
cgcttactgg ggtcagggca ccctggtcac cgtttctgca gggagcacca agggccatc      540 ggtcttcccc ctggcaccct cctccaagag cacctctggg ggcacagcgg ccctgggctg      600
cctggtcaag gactacttcc ccgaaccggt gacggtgtcg tggaactcag gcgccctgac      660
cagcggcgtg cacaccttcc cggctgtcct acagtcctca ggactctact ccctcagcag      720
cgtggtgact gtgccctcca gcagcttggg cacccagacc tacatctgca acgttaatca      780
caaacccagc aacaccaagg tcgacaagaa agttgagccc aaatcttgct aataactaac      840
taaccaagat ctgtacccct tggggcctct aaacgggtct tgaggggttt tttggatccg      900
aattcaccgg tgatatcat                                                   919
```